United States Patent [19]

Batisi et al.

[11] Patent Number: 5,194,602
[45] Date of Patent: Mar. 16, 1993

[54] 9α-HYDROXY-17-METHYLENE STEROIDS, PROCESS FOR THEIR PREPARATION AND THEIR USE IN THE PREPARATION OF CORTICOSTEROIDS

[75] Inventors: Jacobus N. M. Batisi, Kwintsheul; Arthur F. Marx, Delft, both of Netherlands

[73] Assignee: Gist-Brocades N.V., Delft, Netherlands

[21] Appl. No.: 474,852

[22] PCT Filed: Apr. 7, 1989

[86] PCT No.: PCT/NL89/00020
§ 371 Date: Dec. 12, 1990
§ 102(e) Date: Dec. 12, 1990

[87] PCT Pub. No.: WO89/09781
PCT Pub. Date: Oct. 19, 1989

[30] Foreign Application Priority Data

Apr. 8, 1988 [NL] Netherlands ............... 88200675.2

[51] Int. Cl.$^5$ ............... C07J 13/00; C07J 41/00; C07J 5/00
[52] U.S. Cl. ............................... 540/29; 540/30; 540/31; 540/36; 540/38; 540/94; 540/96; 540/97; 552/510; 552/515; 552/519; 552/528; 552/530; 552/562; 552/582; 552/600; 552/601

[58] Field of Search ............... 552/510, 515, 519, 530, 552/562, 582, 600, 601; 540/96, 97, 29, 30, 31, 36, 38, 118; 514/169, 172, 173, 179

[56] References Cited

U.S. PATENT DOCUMENTS

| 3,445,907 | 7/1969 | Dryden et al. | 540/31 |
| 3,461,145 | 8/1969 | Haede et al. | 540/118 |
| 4,462,302 | 8/1984 | Nedelec et al. | 552/601 |
| 4,501,701 | 2/1985 | Barton et al. | 552/582 |

FOREIGN PATENT DOCUMENTS

| 11235 | 5/1980 | European Pat. Off. | 552/530 |
| 23856 | 2/1981 | European Pat. Off. | 552/601 |
| 192288 | 8/1986 | European Pat. Off. | 552/582 |
| 1444656 | 11/1959 | France | 552/530 |
| 2086907 | 5/1982 | United Kingdom | 540/30 |

OTHER PUBLICATIONS

Greene Protective Groups in Organic Synthesis (New York, J. Wiley and Sons, 1981) pp. 133, 144, and 145.

Primary Examiner—Robert T. Bond
Assistant Examiner—E. C. Ward
Attorney, Agent, or Firm—Keck, Mahin & Cate

[57] ABSTRACT

New 9α-hydroxy-17-methylene steroids are prepared by the introduction of a substituted 17-methylene group in 9α-hydroxyandrost-4-ene-3, 17-dione.

The resulting compounds are useful starting compounds in the synthesis of corticosteroids.

7 Claims, No Drawings

9α-HYDROXY-17-METHYLENE STEROIDS, PROCESS FOR THEIR PREPARATION AND THEIR USE IN THE PREPARATION OF CORTICOSTEROIDS

The invention relates to new 9α-hydroxy-17-methylene steroids with a substituted 17-methylene group, to their preparation and to their use in the preparation of corticosteroids.

Nearly all steroids which are currently used as pharmaceuticals originate either directly or indirectly from steroid raw materials found in nature. Originally diosgenin formed the main supply of a raw material. In order to become less dependent of this specific compound investigations have been made to see if other steroids which are abundantly available, e.g. cholesterol, sitosterol, stigmasterol or campesterol could also be used as a starting substance. Microbiological processes were developed to convert in one step said substances into 17-oxo steroids, especially into androst-4-ene-3,17-dione. From the latter compound it was possible to obtain 9α-hydroxyandrost-4-ene-3,17-dione using a second microbiological step. This compound can be prepared even directly from the above-mentioned sterols, for example by using a specific *Mycobacterium fortuitum* strain, see British patent No. GB-A-1530730, or Mycobacterium species, CBS 482.86, see European patent application No. 87202619.0.

For several syntheses which lead to pharmacologically active steroids 9α-hydroxyandrost-4-ene-3,17-dione is a very suitable starting compound, because it is apt to functionalisation in the D-ring, as well as in the C-ring of the steroid nucleus. An important class of steroids containing many pharmacologically active compounds are the pregnanes. The corticosteroids, on the D-ring characterised by the 17β-hydroxyacetyl and 17α-hydroxy substituents (which both may be esterified), are particularly important representatives of this class. Many corticosteroids possess on the C16-position also a α-hydroxyl or a methyl group which is either α- or β-oriented. Multi-step chemical syntheses of pregnanes starting from the readily available above-mentioned 17-oxo steroids are well known in the art as illustrated by J. Org. Chem. 1979, 44, 1582 or by Bull. Chem. Soc. Jpn. 1985, 58, 981 and by its references cited under 3) or Chem. Soc. Rev. 1983, 12, 75 or by U.S. Pat. No. 4,500,461 and by its references cited in its introduction. An important group of syntheses of corticosteroids makes use of steroids with an (optionally substituted) 17-methylene group as starting compounds. These may be prepared from the corresponding 17-oxo steroids by well known methods. In case the starting steroid contains also a 9α-hydroxyl group, the first step is without exception a dehydration to a 9(11)-dehydro steroid. The reason is that the presence of the tertiary 9α-hydroxyl function is assumed to cause undesired rearrangements, especially in the steroid A-ring, as reported by C. G. Bergstrom and R. M. Dodson, Chemistry and Industry 1961, 1530 and L. J. Chinn & R. M. Dodson, J. Org. Chem. 1959, 24, 879. Because 9(11)-dehydro steroids are believed up to now to be more stable, the dehydration of 9α-hydroxy steroids seemed to be an obvious reaction to begin, previous to building a side chain of a corticosteroid. No corticosteroid syntheses are known which take along the 9α-hydroxyl group.

The object of the present invention is to provide starting compounds not earlier used for established routes to the above-said corticosteroids These compounds are 9α-hydroxy-17-methylene steroids of formula I, which has characteristic cyclopentanopolyhydrophenantrene structure possessing angular methyl groups at C10 and C13.

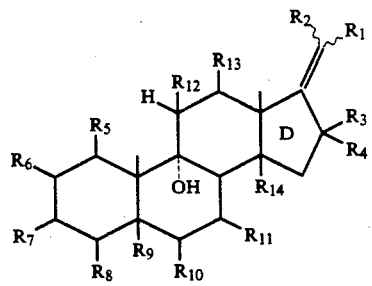

where
R$_1$ is hydrogen, halogen, cyano, isocyano, formamido, (1–6C)alkoxy,
R$_2$ is nitro, methyl, (1–6C)alkoxycarbonyl, hydroxymethyl, (1–6C)alkylcarbonyloxymethyl,
R$_3$ is hydrogen,
R$_4$ is hydrogen, hydroxy, methyl or
R$_3$ and R$_4$ together form methylen
R$_5$ is hydrogen, alkyl or with R$_6$ is a double bond, epoxy, methylene, 3,3-alkylenedioxy, 3,3-alkylenedithio or 3,3-alkyleneoxythio group, the alkylene group preferably containing 2 or 3 carbon atoms,
R$_6$ is hydrogen, alkyl or with R$_5$ is a double bond, epoxy, methylene, 3,3-alkylenedioxy, 3,3-alkylenedithio or 3,3-alkyleneoxythio group, the alkylene group preferably containing 2 or 3 carbon atoms,
R$_7$ is hydrogen, hydroxy, oxo, (1–4C)alkoxy, (1–6C)alkylcarbonyloxy, alkoxyalkoxy, tetrahydropyranyloxy, amino, 3-alkylamino containing 1 through 4 carbon atoms, 3-dialkylamino wherein the alkyl groups are the same or different, each alkyl group containing 1 through 4 carbon atoms, or 3-dialkylamino groups in which the nitrogen atom together with the alkyl groups forms a heterocyclic ring, containing 3 through 8 ring atoms, which ring optionally may contain an oxygen atom, or imino, 3-hydroxyimino, 3-(1–6C)alkoxyimino, 3,3-alkylenedioxy, 3,3-alkylenedithio, 3,3-alkyleneoxythio, the alkylene group preferably containing 2 or 3 carbon atoms, or with R$_5$ is a double bond,
R$_8$ is hydrogen or with R$_7$ or R$_9$ +is a double bond,
R$_9$ is hydrogen or with R$_8$ or R$_{10}$ is a double bond,
R$_{10}$ is hydrogen, halogen or alkyl or with R$_9$ or R$_{11}$ is a double bond,
R$_{11}$ is hydrogen, hydroxy or alkyl or with R$_{10}$ is a double bond,
R$_{12}$ is hydrogen, hydroxy, halogen, alkoxy, alkoxyalkoxy, tetrahydropyranyloxy or with R$_{13}$ is a double bond,
R$_{13}$ is hydrogen, hydroxy, oxo, (1–4C)alkoxy or with R$_{12}$ is a double bond,
R$_{14}$ is hydrogen or hydroxy with the exception of 9α,21-dihydroxypregna-4,17(20)-diene-3,11-dione and the corresponding 21-acetate.

The 20-carbon atom may be in the "zusammen" (Z-) or in the "entgegen" (E-) configuration. R$_4$ may be in the α- or in the β-position.

These 9α-hydroxy-17-methylene steroids are novel compounds with the exception of 9α,21-dihydroxypregna-4,17(20)-diene-3,11-dione and its corresponding 21-acetate, which have been prepared by microbiological 9α-hydroxylation according to FR-A No. 1444656. The latter compounds as such are not comprised within the invention.

The nucleus of 9α-hydroxy steroids of formula I may contain one or more double bonds, a sole double bond being preferably present between C1 and C2, C3 and C4, C5 and C6, C6 and C7, C11 and C12, more preferably the double bond being present either between C4 and C5 or between C5 and C6, and when two or more double bonds are present the following systems are preferred C3–C4 and C5–C6, C4–C5 and C6–C7. and in addition to the 9α-hydroxyl group one or more oxygen or halogen atoms or hydroxyl, amino, hydroxyimino, (1–6C)alkoxyimino, alkyl, alkylene, alkoxy, alkoxyalkoxy,(1–6C)alkylcarbonyloxy, epoxy, methylene, alkylenedioxy, alkylenedithio or alkyleneoxythio groups.

When the rings A, B, C and D of the steroid nucleus are further substituted by a hydroxyl group besides the 9α-hydroxyl group, suitable groups are 3-, 7-, 11-, 12-, 14- or 16-hydroxyl groups.

When the rings A, B, C and D are substituted by an amino group, suitable amino groups are 3-alkylamino groups, preferably containing 1 through 4 carbon atoms, 3-dialkylamino groups wherein the alkyl groups are the same or different, each alkyl group preferably containing 1 through 4 carbon atoms, or 3-dialkylamino groups in which the nitrogen atom together with the alkyl groups forms a heterocyclic ring, preferably containing 3 through 8 ring atoms, which ring optionally may contain an oxygen atom, particularly preferred are dimethylamino, diethylamino, pyrrolidino and morpholino substituents.

When the rings A, B, C and D are substituted by an imino group, suitable imino groups are the 3-hydroxyimino group or a 3-(1–6C)alkoxyimino group.

When the rings A, B, C and D are substituted by an oxo group this group is preferably present at C3, C11 or C12, more preferably as the 3-oxo-4(5)-dehydro function.

When the rings A, B, C and D are substituted by a halogen atom, suitable halogen substituents are 6- or 11-fluorine, -chlorine or -bromine atoms, preferably 6-fluorine or 6-chlorine atoms.

When the rings A, B, C, and D are substituted by an alkyl group, suitable alkyl groups are 1-, 2-, 6- or 7-methyl groups, preferably 6- and 16-methyl.

When the rings A, B, C and D are substituted by an alkoxy group, suitable alkoxy groups are 3-, 11- or 12-alkoxy groups containing 1 through 4 carbon atoms, preferably 3- or 11-methoxy or ethoxy groups.

When the rings A, B, C and D are substituted by an (1–6C)alkylcarbonyloxy group, preferably it is substituted on C3. The preferred group is acetoxy.

When the rings A, B, C and D are substituted by an alkoxyalkoxy group, suitable groups are 3- or 11-methoxymethoxy, methoxyethoxy or tetrahydropyranyloxy groups.

When the rings A, B, C and D are disubstituted, suitable substituents are an epoxy group at C1 and C2 or a methylene group attached to C1 and C2 or a 3,3-alkylenedioxy, a 3,3-alkylenedithio or a 3,3-alkyleneoxythio group, the alkylene group preferably containing 2 or 3 carbon atoms.

A particular group of 9α-hydroxy-17-methylene steroids are those indicated with formula I in which $R_1$ is formamido or cyano and $R_2$ is (1–6C)alkoxycarbonyl, hydroxymethyl or (1–6C)alkylcarbonyloxymethyl.

Another group of interest of 9α-hydroxy-17-methylene steroids are those indicated with formula I in which $R_1$ is halogen or (1–6C)alkoxy and $R_2$ is (1–6C)alkoxycarbonyl or hydroxymethyl or (1–6C)alkylcarbonyloxymethyl.

Another group of interest of 9α-hydroxy-17-methylene steroids are those indicated with formula I in which $R_1$ is hydrogen and $R_2$ is methyl or nitro.

Another group of favourable 9α-hydroxy-17-methylene steroids are those indicated with formula I where $R_1$ is isocyano or formamido and $R_2$ is methyl.

The 17-methylene steroids as defined above have as a common denominator, that they are suitable starting compounds in synthetic routes to the corticosteroids as defined above, using known methods by analogy.

The invention is based on the finding that a new approach to the synthesis of corticosteroids has been made available in that use is made of substituted 17-methylene steroids in which the 9α-hydroxyl group is a characteristic novel feature.

The following compounds are particularly preferred starting compounds in the synthesis of corticosteroids:
1. (1–6C)alkyl 20-formamido-9α-hydroxy-3-oxopregna-4,17(20)-dien-21-oate
2. 20-formamido-9α,21-dihydroxypregna-4,17(20)-dien-3-one
3. (1–6C)alkyl 20-chloro-9α-hydroxy-3-oxopregna-4,17(20)-dien-21-oate
4. (1–6C)alkyl 20-(1–6C)alkoxy-9α-hydroxy-3-oxopregna-4,17(20)-dien-21-oate
5. 20-(1–6C)alkoxy-9c,21-dihydroxypregna-4,17(20)-dien-3-one
6. 21-(1–6C)alkylcarbonyloxy-20-(1–6C)alkoxy-9α-hydroxypregna-4,17(20)-dien-3-one
7. 9α-hydroxy-17-nitromethyleneandrost-4-en-3-one
8. 9α-hydroxypregna-4,17(20)-dien-3-one
9. 9α-hydroxy-20-isocyanopregna-4,17(20)-dien-3-one
10. 20-formamido-9α-hydroxypregna-4,17(20)-dien-3-one
11. (1–6C)alkyl 20-cyano-9α-hydroxy-3-oxo-pregna-4,17(20)-dien-21-oate in which compounds the function on C3 may be properly protected and C16 may be substituted by a methyl, a methylene or a hydroxyl group.

The use of the new 9α-hydroxy-17-methylene steroids as starting compounds in the synthesis of pharmacologically active pregnanes, especially corticosteroids, has important advantages, particularly:

1. When dehydration is desired, for example as a first step in the functionalisation of the C11-atom, it is economical to combine in a single reaction the dehydration with one or more concomitant steps in the synthesis, e.g. the step of deprotection of protected functional groups, using e.g. acid hydrolysis of the protected 3-oxo substituent.

2. Several reactions which cannot be carried out with a 9(11)-double bond, or only with a poor yield, proceed in good yields when the corresponding 9α-hydroxy compound is used as a starting compound. An example of such reaction is the epoxidation of the 17(20)-methylene bond as shown in charts I and M, which equally will attack the 9(11)-double bond.

While the prior art only provides microbiological methods for the preparation of 9α-hydroxy steroids, consisting in microbiological 9α-hydroxylations, see e.g. U.S. Pat. No. 4,397,947, it has now surprisingly been. found that these 9α-hydroxy steroids can be prepared easily from other 9α-hydroxy steroids using chemical reactions known in the art. These reactions are until now supposed to be aggressive for the 9α-hydroxyl group of said steroids. Most reactions, however, can be carried out, necessitating only by exception particular precautions to spare the 9α-hydroxyl group, since this group has been discovered to be unexpectedly stable and to be affected only in case reaction conditions are present which are either extreme, or which are chosen specifically to bring about a modification of the 9α-hydroxyl group.

Therefore according to a further aspect of this invention it is possible to prepare 9α-hydroxy-17-methylene steroids and subsequently 9α-hydroxypregnanes commencing with the corresponding 9α-hydroxy-17-oxo steroid.

An important group of 9α-hydroxy-17-oxo steroids which are suited for the preparation of the compounds according to the invention are the above-mentioned 9c-hydroxy-17-oxo steroids obtained by microbiological sterol degradation. Preferably 9α-hydroxyandrost-4-ene-3,17-dione is used.

The 9α-hydroxy-17-methylene steroids of the invention may be prepared by analogous processes such as those described in general textbooks as are e.g. Steroid Reactions, edited by Carl Djerassi (1962) or Fried and Edwards, Organic Reactions in Steroid Chemistry (1972) or in Chem. Soc. Rev. 1983, 12, 75.

The invention compounds are used in processes suited for the subsequent conversion of the 17-methylene substituent into the C17 groups which are characteristic for corticosteroids. The introduction of a substituent on C16 should be carried out before conversion of the 17-oxo to the 17-substituted methylene group. Suited processes may be found in comprehensive review literature such as Organic Reactions in Steroid Chemistry Vol. 2, chapters 10 and 11 and moreover in specific patent literature, e.g. GB-A No. 2086907 and U.S. Pat. No. 4,216,159.

Sensitive substituents, especially the 3-oxo function, are to be protected in the usual way by known protecting groups. For the oxo substituent in 3-oxo-4(5)-dehydro steroids many protecting groups are available. Examples of protecting groups for the 3-oxo-function, either combined with a 4(5) double bond or not, are (1-4C) alkyoxy, (1-6C) alkylcarbonyloxy, alkoxyalkoxy, tetrahydropyranyloxy, amino, 3-alkylamino containing 1 through 4 carbon atoms, 3-dialkylamino wherein the alkyl groups are the same or different, each alkyl group containing 1 through 4 carbon atoms, or 3-dialkylamino groups in which the nitrogen atom together with the alkyl groups forms a heterocyclic ring having 3 through 6 ring atoms, or 3-morpholino imino, 3-hydroxyimino, 3-(1-6C) alkoxyimino, 3,3-alkylenedioxy, 3,3-alkylenedithio, 3,3-alkyleneoxythio and the alkylene group containing 2 or 3 carbon atoms. It is preferably protected as enol ether, ketal or enamine by methods well known in the art. The preferred enol ether is the methyl or ethyl ether. The preferred ketal is the ethylene ketal; also the ethylenethio ketal has appeared to be useful. The preferred enamines are selected from the group consisting of pyrrolidino, morpholino and diethylamino amines. The enol ethers are prepared according to e.g. J. Org. Chem. 1961, 26, 3925, Steroid Reactions, supra 42–45, and U.S. Pat. No. 3,516,991. The ketals are prepared according to e.g. Steroid Reactions, supra, 3–35. The 3-enamines are prepared according to e.g. Steroid Reactions, supra, 49–53.

Although the 9α-hydroxyl group is stable enough to withstand a variety of reaction conditions, it can be eliminated under rather extreme conditions. Therefore one should avoid for example heating for a prolonged time at high or low pH values. It can be easily determined whether actual reaction conditions are detrimental to the maintenance of the 9α-hydroxyl group. Spectrophotometrically (1H NMR, 13C NMR, IR) or chromatographically (TLC, HPLC) it can be easily proved that the 9α-hydroxyl group is retained in an obtained product.

The invention comprises at least the following types of reactions for preparing the new 9α-hydroxy-17-methylene steroids. They are presented by way of illustration and should not be conceived as a limitation of the invention: A. When reacting a 9α-hydroxy-17-oxo steroid III with a (1-6C)alkyl isocyanoacetate in an anhydrous polar aprotic solvent in the presence of a strong base according to Chem. Ber. 1976, 109, 3964 a 17-[(1-6C)alkoxycarbonylformamidomethylene] steroid IV still containing the 9α-hydroxyl group is obtained (chart A). Preferably the reagent is methyl or ethyl isocyanoacetate, the base is an alkali metal alkoxide such as potassium tert. butoxide and the solvent is tetrahydrofuran.

When treating a 17-[(1-6C)alkoxycarbonylformamidomethylene]-9α-hydroxy steroid IV with a reducing agent according to J. Chem. Soc. Chem. Comm. 1981, 775 or EP-A No. 0023856 a 17-(formamidohydroxymethylmethylene) steroid V still containing the 9α-hydroxyl group is obtained (chart A). The reducing agent may be a complex metal hydride such as lithium aluminium hydride or an alkali metal dihydro-bisalkoxyaluminate such as sodium dihydrobis(2-methoxyethoxy)-aluminate. Preferably the reaction is carried out with lithium aluminium hydride. To improve the reduction yield sodium borohydride or potassium borohydride may be added to the reaction mixture thus reducing small amounts of intermediate aldehyde.

When treating a 17-(formamido-hydroxymethylmethylene)-9α-hydroxy steroid V with an anhydride (R-CO)₂O, or an acyl chloride R—COCl, where R is (1-6-C)alkyl, or another agent for introducing a carboxylic ester group RC(O)O— according to J. Chem. Soc. Chem. Comm. 1981, 775 or EP-A No. 0023856 a 17-[(1-6C)alkylcarbonyloxymethyl-formamidomethylene] steroid VI still containing the 9α-hydroxyl group is obtained (chart A). Preferably acetic anhydride with pyridine as solvent is used as esterifying agent thus obtaining a 17-(acetoxymethyl-formamidomethylene)-9α-hydroxy steroid VI (R is methyl).

When reacting a 9α-hydroxy-17-oxo steroid III with a (1-6C)alkyl trichloroacetate, such as methyl or ethyl trichloroacetate, in the presence of zinc dust and diethylaluminium chloride according to J. Org. Chem. 1982, 47, 2993 a 17-[(1-6C)alkoxycarbonyl-chloromethylene] steroid VII still containing the 9c-hydroxyl group is obtained (chart B). The reaction is carried out preferably in a polar aprotic solvent such as tetrahydrofuran or methyl trichloroacetate in tetrahydrofuran and the reaction product is a 17-(chloromethoxycarbonylmethylene)-9α-hydroxy steroid VII (R is methyl and X=chloro).

When a 17-[(1-6C)alkoxycarbonyl-chloromethylene]-9α-hydroxy steroid VII is treated with an alkali metal (1-6C)alkoxide, such as sodium ethoxide or sodium methoxide according to J. Org. Chem. 1982, 47, 2993, a 17-[(1-6C)alkoxy-(1-6C)alkoxycarbonylmethylene] steroid o VIII still containing the 9α-hydroxyl group is obtained (chart B). The reaction is carried out in the (1–6C)dimethoxyethane. alcohol corresponding with the alkoxide. Preferably, the reaction is carried out with sodium methoxide in methanol thus obtaining a 17-(methoxycarbonyl-methoxymethylene)-9α-hydroxy steroid VIII (R' is methyl).

When a 17-[(1–6C)alkoxy-(1–6C)alkoxycarbonylmethylene]-9α-hydroxy steroid VIII is treated with a reducing agent according to J. Org. Chem. 1982, 47, 2993, a 17-[(1–6C)alkoxy-hydroxymethylmethylene] steroid IX still containing the 9α-hydroxyl group is obtained (chart B). The reducing agent may be a complex metal hydride such as lithium aluminium hydride or diisobutylaluminium hydride. Preferably the reaction is carried out with diisobutylaluminium hydride as reducing agent in an inert aprotic solvent, such as tetrahydrofuran, preferably in toluene.

The hydroxymethyl group of a 17[(1–6C)alkoxyhydroxymethylmethylene]-9α-hydroxy steroid IX is acylated, for instance by treatment with a (1–6C)- alkylcarbonyl chloride R—COCl, where R=(1–6C)alkyl, or with a corresponding anhydride, (RCO)$_2$O, preferably with acetic anhydride in pyridine, to obtain a 17-[(1–6C)alkoxy-(1–6C)alkylcarbonyloxymethylmethylene] steroid X still containing the 9α-hydroxy group (chart B). All products are in the Z-configuration, except compound VII which is in the E-configuration.

C. When reacting a 9α-hydroxy-17-oxo steroid III with a (1–6C)alkyl (1–6C)alkoxydihaloacetate, preferably methyl or ethyl methoxydichloroacetate, in the presence of zinc dust and diethylaluminium chloride, in a polar aprotic solvent such as tetrahydrofuran, according to Synthesis 1984, 132, a 17-[(1–6C)alkoxy-(1–6C)alkoxycarbonylmethylene] steroid XI still containing the 9α-hydroxyl group is obtained (chart C).

When a 17-[(1–6C)alkoxy-(1–6C)alkoxycarbonylmethylene]-9α-hydroxy steroid XI is treated with a reducing agent according to Synthesis 1984, 132 a 17-[(1–6C)alkoxyhydroxymethylmethylene] steroid XII still containing the 9α-hydroxyl group is obtained (chart C). The reducing agent may be a complex metal hydride such as lithium aluminium hydride or diisobutylaluminium hydride. Preferably the reaction is carried out with diisobutylaluminium hydride as reducing agent in an inert aprotic solvent such as tetrahydrofuran, preferably toluene. If desired the product of formula XII is acylated as described under B, to obtain a 17-[(1–6C)alkoxy-(1–6C)alkylcarbonyloxymethylmethylene] steroid X still containing the 9α-hydroxy group. All products are in the E-configuration.

D. When refluxing a 9α-hydroxy-17-oxo steroid III in nitromethane in the presence of a catalytic amount of ethylenediamine, propylenediamine or asymmetric N,N-dimethylethylenediamine, preferably ethylenediamine, according to J. Chem. Soc. Chem. Comm. 1982, 551, Bull. Soc. Chim. France 1983, II-61 or EP-A No. 0192288 a 17-(nitromethylene) steroid XIII still containing the 9α-hydroxyl group is obtained (chart D).

E. When reacting a 9α-hydroxy-17-oxo steroid III with an ethylidene Wittig reagent such as ethylidenetriphenylphosphorane in the presence of a base in an anhydrous polar aprotic solvent according to J. Org. Chem., 1966, 31, 24 or Helv. Chim. Acta 1984, 67, 612 and references included in it, a 17-(methylmethylene) steroid XIV still containing the 9α-hydroxyl group is obtained (chart E). The base may be an alkali metal alkoxide, such as potassium tert. butoxide or sodium ethoxide, or a metal hydride, such as sodium hydride. Examples of polar aprotic solvents are tetrahydrofuran, dimethylsulfoxide and toluene. Preferably the reaction is carried out with ethylidenetriphenylphosphorane with potassium tert. butoxide or sodium hydride as base and tetrahydrofuran or dimethylsulfoxide as solvent.

F. When reacting a 9α-hydroxy-17-oxo steroid III in a polar aprotic solvent with a (1–6C)dialkyl α-isocyanoethylphosphonate, preferably with diethyl α-isocyanoethylphosphonate, in the presence of a strong base according to Nouveau Journal de Chimie 1982, 6, 295, or GB-A No. 2079756 a 17-(isocyano-methylmethylene) steroid XV still containing the 9α-hydroxyl group is obtained (chart F). The strong base may be an alkali metal alkoxide, such as potassium tert. butoxide or sodium ethoxide, or a metal hydride, such as sodium hydride. Examples of polar aprotic solvents are tetrahydrofuran and dimethoxyethane. It is preferred to carry out the reaction with potassium tert. butoxide as base and tetrahydrofuran as solvent.

When hydrating a 17-(isocyano-methylmethylene)-9α-hydroxy steroid XV in an acidic medium according to Nouveau Journal de Chimie, 1982, 6, 295, or GB-A No. 2079756 a 17-(formamido-methylmethylene) steroid XVI, still containing the 9α-hydroxyl group is obtained (chart F). Examples of acidic medium are acetic, propionic, oxalic or formic acid. Preferably, the hydration is carried out in formic acid.

G. When reacting a 9α-hydroxy-17-oxo steroid III with a (1–6C)alkyl cyanoacetate, preferably ethyl or methyl cyanoacetate, in the presence of a catalyst, according to Chem. Ber. 1978, 111, 1533 a 17-[(1–6C)alkoxycarbonylcyanomethylene] steroid XVII still containing the 9α-hydroxyl group is obtained (chart G). The catalyst is selected from the group used for Knoevenagel condensations and described for instance by Jones in Organic Reactions 1967, 15, chapter 2 (edited by Adams et al.). Examples of these catalysts are organic amines, such as pyridine and benzylamine, ammonium or amine acetates such as piperidinium acetate, alkali metal hydroxides, such as sodium hydroxide and amino acids such as β-alanine. Potassium fluoride and titanium tetrachloride are also used as catalysts. Preferably potassium fluoride or β-alanine with acetic acid are used, more preferably potassium fluoride. Reaction conditions depend on the nature of the 9α-hydroxy-17-oxo steroid and on the catalyst used, as teached further in Organic Reactions, supra 264–273. With potassium fluoride as catalyst e.g. it is preferred to carry out the reaction in ethanol in a sealed vessel at a temperature between 80°–130° C., more preferably between 100°–120°C.

H. The introduction of a methyl group on the C16-atom of a 9α-hydroxy steroid is an especially important process in that it is a step in the preparation of a useful type of corticosteroids comprising betamethason and dexamethason. The reaction is carried out either in one step or via the corresponding 16-methylene compound. The introduction should preferably be carried out before the earlier described reactions on the 17-oxo group. In any case it is necessary to protect first properly reactive functions such as the reactive 3-oxo-4(5)-dehydro function.

The direct introduction of a 16-methyl substituent is described in e.g. EP-A No. 0115965 and in the included references to older methods. By analogy one or more of the steps of the following reaction sequence are used:

1. A properly 3-oxo protected 9α-hydroxy steroid containing a D-ring according to formula XVIII

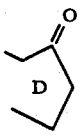   XVIII is reacted with a C16-activating agent selected from di(1–3C)alkyl oxalates, (1–3C)alkyl formates or di(1–3-C)alkyl carbonates in the presence of an alkali metal (1–3C)alkoxide, such as lithium, sodium or potassium alkoxides preferably sodium methoxide and sodium ethoxide.

2. The product of step 1 is reacted with a methylating agent such as methyl iodide or methyl bromide, 3. The product of step 2 is reacted with a strong base in a solvent containing a (1–6C)alkanol, preferably methanol, to give the corresponding 9α-hydroxy steroid containing a D-ring according to formula III

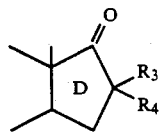   III where $R_3$ is hydrogen and $R_4$ is β-methyl. Strong bases include, for example, alkali metal alkoxides, such as sodium methoxide, alkali metal hydroxides, such as sodium hydroxide and alkali metal carbonates, such as potassium carbonate.

The introduction of a 16-methylene function is teached by G. Schneider et al., Synthesis 1983, 665 and in U.S. Pat. No. 4,416,821. A way to reduce the methylene group to a methyl group is found in U.S. Pat. Nos. 3,130,209 and 3,115,508, yielding compounds with respectively a 16α-methyl and a 16β-methyl substituent. One may proceed e.g. as follows using one or more of the following steps:

1. reacting a C3-protected 9α-hydroxy steroid containing a D-ring according to formula XVIII

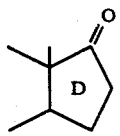   XVIII with a C16-activating agent selected from di(1–3C)alkyl oxalates, (1–3C)alkyl formates or di(1–3C)alkyl carbonates in the presence of an alkali metal (1–3C)alkoxide such as sodium or potassium alkoxides, preferably sodium methoxide or sodium ethoxide, 2. reacting the product of step 1 with formaldehyde or a formaldehyde generating agent such as paraformaldehyde, to give the corresponding 9α-hydroxy steroid containing a D-ring according to formula XIX

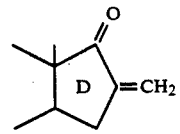   XIX 3. reacting the product of step 2, with a reducing agent such as palladium on carbon, to give the corresponding 9α-hydroxy steroid containing a D-ring according to formula III

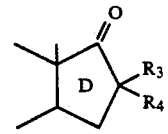   III where $R_3$ is hydrogen, $R_4$ is α-methyl or β-methyl.

In spite of rather severe reaction conditions the 9α-hydroxyl group re-appears unaltered in the product. The obtained 9α-hydroxy-16-methyl-17-oxo or 9α-hydroxy-16-methylene-17-oxo steroid can be converted further into the corresponding 17-methylene compound of the invention, using e.g. one of the methods mentioned under A-G.

The new 9α-hydroxy-17-methylene steroids according to this invention are useful starting compounds especially for the preparation of pharmacologically active pregnanes, particularly corticosteroids as defined before, and more particularly steroids containing a D-ring according to formula XX:

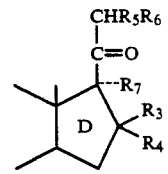   XX where
$R_5$ is hydrogen, halogen, optionally substituted benzoate, hydroxy, optionally halogenated (1–6C)alkylcarbonyloxy,
$R_6$ is hydrogen or halogen,
$R_7$ is hydrogen or optionally protected hydroxy,
$R_3$ is hydrogen,
$R_4$ is hydrogen, hydroxy, methyl or
$R_3$ and $R_4$ together form methylene or
$R_7$ and $R_3$ together form a double bond.

The processes for obtaining these corticosteroids characterised by the use of the new 9α-hydroxy-17-methylene steroids are also part of this invention. Intermediate compounds will bear the 9α-hydroxyl group preferably as long as possible until it will be removed by a 9(11)-dehydration reaction.

For the preparation of said pregnanes, particularly the corticosteroids and the intermediates for their preparation, the following methods are particularly useful:

1. When hydrolysing a 17-(formamido-hydroxymethyl-methylene)-9α-hydroxy steroid V under acidic conditions according to J. Chem. Soc. 1981, 775 a 9α,21-dihydroxy-20-oxo pregnane XXIV is obtained (chart H). Examples of acidic conditions are mixtures of aqueous hydrochloric acid, sulfuric acid or perchloric acid, with a water miscible organic solvent such as methanol or tetrahydrofuran.

When reacting a 17-[(1–6C)alkylcarbonyloxymethylformamidomethylene-]-9α-hydroxy steroid VI with a (1–6C)alkylcarbonyloxylating agent, according to J. Chem. Soc. 1981, 775 or EP-A No. 0058097 a 17,21-di(-1–6C)alkylcarbonyloxy-20-formyliminopregnane XXI, still containing the 9α-hydroxyl group is obtained (chart H). Preferably steroid VI is a 17-(acetoxymethylformamidomethylene)-9α-hydroxy steroid and the alkylcarbonyloxylating agent is an acetoxylating agent, such as lead tetraacetate or iodosobenzene diacetate, more preferably lead tetraacetate. The reaction is preferably carried out in an anhydrous polar organic solvent such as benzene or toluene.

When hydrolysing a 17,21-di(1–6C)alkylcarbonyloxy-20-formylimino-9α-hydroxypregnane XXI under acidic conditions according to J. Chem. Soc. 1981, 775 or EP-A No. 0058097 a 17,21-di(1–6C)alkylcarbonyloxy-20-oxopregnane XXII, still containing the 9α-hydroxyl group is obtained (chart H). Examples of acidic conditions are mixtures of aqueous hydrochloric acid, sulfuric acid or perchloric acid. Other conditions are aqueous carboxylic acids such as aqueous acetic acid. Preferably a 17,21-diacetoxy-20-formylimino-9α-hydroxypregnane is converted into a 17,21-diacetoxy-9α-hydroxy-20-oxopregnane. It is preferred to carry out the hydrolysis in aqueous acetic acid.

Optionally a 17,21-di(1–6C)alkylcarbonyloxy-9α-hydroxy-20-oxo- pregnane XXII is saponified using methods known in the art thus obtaining a 9α,17α,21-trihydroxy-20-oxopregnane XXIII. Preferably the 9α-hydroxy steroid XXII is treated under nitrogen with a base such as sodium methoxide or potassium hydroxide, followed by treatment with an acid such as hydrochloric acid, sulfuric acid or acetic acid.

2. When reacting a 17-[(1–6C)alkoxyhydroxymethylmethylene]-9α-hydroxy steroid IX or XII with an oxidizing agent according to J. Org. Chem. 1982, 47, 2993 or Synthesis 1984, 132 a 9α,17α,21-trihydroxy-20-oxopregnane XXIII is obtained (chart I). The oxidation is preferably carried out with a peracid, for example metachloroperbenzoic acid, perphtalic acid, peracetic acid or performic acid. More preferably metachloroperbenzoic acid is used.

When hydrolysing a 17-[(1–6C)alkoxyhydroxymethylmethylene]-9α-hydroxy steroid IX or XII under acidic conditions according to J. Org. Chem. 1982, 47, 2993 or Synthesis 1984, 132 a 9α,21-dihydroxy-20-oxopregnane XXIV is obtained (chart I). Examples of acidic conditions are mixtures of aqueous hydrochloric acid, sulfuric acid or perchloric acid with a water miscible organic solvent such as methanol or tetrahydrofuran. Preferably, aqueous perchloric acid and methanol are used.

3. When oxidizing a 17-[(1–6C)alkoxy-(1–6C)alkylcarbonyloxymethylmethylene]-9α-hydroxy steroid X with singulet oxygen according to Chem. Ber. 1980, 113, 1184 a 20-(1–6C)alkoxy-21-(1–6C)alkylcarbonyloxy-20-hydroperoxypregn-16-ene XXV, still containing the 9α-hydroxyl group is obtained (chart J). Methods of producing singulet oxygen are well known in the art and described for instance by Denny and Nickon, Organic Reactions 1973, 20, 133–336. This review deals with sensitized photo oxygenation of olefins and includes usable reaction conditions. The photo oxygenation is preferably carried out in methylene chloride in the presence of a photo sensitizer such as methylene blue.

When reducing a 20-(1–6C)alkoxy-21-(1–6C)alkylcarbonyloxy-20-hydroperoxy-9α-hydroxypregn-16-ene XXV with triphenylphosphine according to Chem. Ber. 1980, 113, 1184 a 21-(1–6C)alkylcarbonyloxy-20-oxopregn- 16-ene XXVI still containing the 9α-hydroxyl group is obtained (chart J).

4. When reacting a 9α-hydroxy-17-nitromethylene steroid XIII with formaldehyde or a formaldehyde generating agent such as paraformaldehyde in the presence of a base such as triethylamine according to Bull. Soc. Chim. France 1983, II-61 or EP-A No. 0192288 a 9α,21-dihydroxy-20-nitro-pregn-16-ene XXVII is obtained (chart K). The reaction is carried out in a water miscible solvent such as tetrahydrofuran, methanol, ethanol or 2-propanol. It is preferred to carry out the reaction in 2-propanol with an aqueous formaldehyde solution and triethylamine as a base.

Optionally a 9α,21-dihydroxy-20-nitropregn-16-ene XXVII is esterified by reaction e.g. with an anhydride $(R-CO)_2O$ or an acyl chloride $R-COCl$ ($R=(1-6C)$alkyl) in the presence of an organic base such as pyridine or dimethylaminopyridine. Analogous to Bull. Soc. Chim. France 1983, II-61 or EP-A No. 0192288 a 21-(1–6C)alkylcarbonyloxy-20-nitropregn-16-ene XXVIII, still containing the 9α-hydroxyl group is obtained (chart K). It is preferred to acetylate the hydroxyl group, whereby the reagent of choice is acetic anhydride with 4-dimethylaminopyridine as a base.

When a 21-(1–6C)alkylcarbonyloxy-9α-hydroxy-20-hydroxyiminopregn-16-ene XXVIII is treated with an aqueous solution of chromous chloride according to J. Chem. Soc. (C) 1970, 1182 or Bull. Soc. Chim. France 1983, II-61, the nitro group will be converted into a hydroxyimino group and a 21-(1–6C) alkylcarbonyloxy-20-hydroxyiminopregn-16-ene XXIX, still containing the 9α-hydroxyl group will be obtained (chart K). At choice the reaction is carried out at room temperature. At this temperature the reaction time preferably is chosen short, i.e. less than 5 minutes. More preferred the reaction time is in the range of 30 to 60 seconds.

When a 21-(1–6C)alkylcarbonyloxy-9α-hydroxy-20-hydroxyiminopregn-16-ene XXIX is treated with aqueous titanium trichloride according to Bull. Soc. Chim. France 1983, II-6 or EP-A No. 0192288 a 21-(1–6C)alkylcarbonyloxy-20-oxopregn-16-ene XXVI still containing the 9α-hydroxyl group is obtained (chart K). The reaction is carried out in a water miscible solvent such as acetone. The reaction is preferably carried out with an aqueous solution of titanium trichloride in a mixture of ammonium acetate, acetic acid and acetone.

5. When treating a 9α-hydroxy-17-(methylmethylene)-steroid XIV with nitrosyl chloride, followed by treatment with a solution of triethylamine in a mixture of tetrahydrofuran and water according to J. Chem. Soc. Perkin Trans. I 1985, 2191 a 20-hydroxyiminopregn-16-ene XXXI still containing the 9α-hydroxyl group is obtained (chart L).

When treating a 9α-hydroxy-20-hydroxyiminopregn-16-ene XXXI with iron powder in a (1–6C)alkylcarboxylic acid such as acetic acid or propionic acid according to J. Chem. Soc. Perkin Trans. I 1984, 2191 a 20-di(1–6C)Perkin alkylcarbonylaminopregna-16,20-diene XXXII, still containing the 9α-hydroxyl group is obtained (chart L). Preferably acetic acid is used as carboxylic acid thus preparing a 20-diacetylamino-9α-hydroxypregna-16,20-diene (XXXII, R is methyl).

When treating a 20-di(1–6C)alkylcarbonylamino-9α-hydroxypregna-16,20-diene XXXII with alumina according to J. Chem. Soc. Perkin Trans. I 1975, 1237 a 20-(1–6C)alkylcarbonylaminopregna-16,20-diene XXXIII, still containing the 9α-hydroxyl group is obtained (chart L). The reaction is carried out by a simple adsorption on a column of alumina. Preferably a 20-diacetyl compound is converted into a 20-acetylamino-9α-hydroxypregna-16,20-diene (XXXIII, R is methyl).

When hydrolysing a 20-(1–6C)alkylcarbonylamino-9α-hydroxypregna-16,20-diene XXXIII under acidic conditions according to Nouveau Journal de Chimie 1982, 6, 295 a 20-oxo-pregn-16-ene XXXIV still containing the 9α-hydroxyl group is obtained (chart L). Examples of acidic conditions are mixtures of aqueous hydrochloric acid, sulfuric acid or perchloric acid with water miscible organic solvents such as methanol or tetrahydrofuran. Other conditions are aqueous hydrocarbon acids such as aqueous acetic acid.

6. When hydrolysing a 17-(isocyano-methylmethylene)-9α-hydroxy steroid XV in an acidic medium according to Nouveau Journal de Chimie 1982, 6, 295 a 9α-hydroxy-20-oxopregnane XXXV is obtained (chart M). The hydrolysis is carried out in a mixture of aqueous hydrochloric acid, sulfuric acid or perchloric acid, with a water miscible organic solvent such as methanol or tetrahydrofuran. Preferably, the reaction is carried out in a mixture of aqueous hydrochloric acid and tetrahydrofuran.

When a 17-(formamido-methylmethylene)-9α-hydroxy steroid XVI, is treated with an epoxidising agent, followed by acid hydrolysis and saponification of the 17-formyloxy group according to Nouveau Journal de Chimie 1982, 6, 295 or GB-A No. 2079756 a 9α,17α-dihydroxy-20-oxopregnane XXXVI is obtained (chart M). The epoxidation is preferably carried out with a peracid, for example meta-chloroperbenzoic acid, perphtalic acid or peracetic acid. Acid hydrolysis is carried out with aqueous hydrochloric acid or aqueous acetic acid. Preferred is aqueous acetic acid. Saponification is carried out with aqueous inorganic bases such as potassium bicarbonate or sodium hydroxide. The hydrolysis and saponification is preferably carried out without isolation of the intermediate 9α-hydroxy steroids. The starting 9α-hydroxy steroid XVI is preferably prepared by hydration of a 17-(isocyano-methylmethylene)-9α-hydroxy steroid XV, for instance by treatment with formic acid, directly followed by the epoxidation, hydrolysis and saponification as described above.

When a 17-(formamido-methylmethylene)-9α-hydroxy steroid XVI is treated with an epoxidizing agent, directly followed by a dehydration reaction according to Nouveau Journal de Chimie 1982, 6, 295 or GB-A No. 2086907 a 17-spiro- 5′-(4′-methylene-4′H-oxazole) steroid XXXVII still containing the 9α-hydroxyl group is obtained. The epoxidation is preferably carried out with a peracid, for example meta-chloroperbenzoic acid, perphtalic acid, peracetic acid or performic acid. More preferred is metachloroperbenzoic acid. The dehydration reaction deals with the conversion of the intermediate 17-spiro-5′-(2′-hydroxy-4′-methyl-2′H-oxazole) fragment (LX) into the 17-spiro-5′-(4′-methylene-4′H-oxazole) fragment (chart M). This result is obtained by azeotropically removal of water by addition and subsequent evaporation of toluene.

When under anhydrous conditions a 9α-hydroxy-17-spiro-5′-(4′-methylene-4′H-oxazole) steroid XXXVII is treated with a halogenating agent such as a chlorinating, brominating or iodinating agent, preferably a brominating agent, more preferably pyridinium bromide perbromide, followed by hydrolysis in acidic medium such as aqueous acetic acid according to Nouveau Journal de Chimie 1982, 6, 295 or GB-A No. 2086907 (1982) a 21-halo-17α-formyloxy-20-oxopregnane XXXVIII still containing the 9α-hydroxyl group is obtained (chart M). It is preferred to carry out the halogenation without isolation of the intermediate 17-spiro-oxazole XXXVII. Optionally saponification of the 17α-formyloxy group is carried out, using inorganic bases such as potassium bicarbonate or sodium hydroxide to obtain a 21-halo-9α,17α-dihydroxy-20-oxopregnane XXXIX (chart M).

One of the reactions which may form a part of the route to corticosteroids is the dehydration of the 9α-hydroxy steroids of this invention, resulting in the corresponding 9(11)-dehydro steroids. The reaction may be carried out directly with the new compounds of the invention or as a subsequent step in the further synthesis, preferably in combination with another reaction step.

Optionally the new 9α-hydroxy steroids are dehydrated by methods known in the art, e.g. according to DE-A No. 2814747 using sulfuric acid treatment or as described in U.S. Pat. No. 4,102,907 via a 9α-sulfinate ester. According to EP-A No. 0253415 or EP-A No. 0294911 suitable methods are teached using silica gel with p-toluenesulfonic acid or using a Lewis acid, such as borium trifluoride.

When the dehydration reaction to a 9(11)-dehydro steroid takes place concomitantly with another step of the synthesis, this happens e.g. with the deprotection of a protected substituent on C3. For example treatment with sulfuric acid of a 9α-hydroxy-17-methylene steroid bearing a 3,3-ethylenedioxy substituent yields in one step a 3-oxo-9(11)-dehydro steroid. The 9(11)-dehydrated products are usually known compounds, being suited for the introduction of pharmacologically interesting substituents, for example the 11-hydroxyl group and/or a 9-halogen atom.

9(11)-Dehydration of the 9α-hydroxy compounds prepared according to the invention may be used too for confirmation of the structure of these compounds by comparing the physical data of the obtained 9(11)-dehydro steroid with those of known compounds with identical structure.

The invention is illustrated by the following examples. For all preparations the presence of the 9α-hydroxyl group has been confirmed by $^{13}$C NMR. NMR-spectra are recorded with 360 MHz proton NMR and with 90 MHz $^{13}$C NMR.

The NMR data are reported in δ (ppm) units downfield from TMS as internal standard.

The IR data are reported in reciprocal centimeters (cm$^{-1}$) All percentages are by weight unless otherwise stated.

EXAMPLE 1

3,3-Ethylenedioxy-17-(nitromethylene)androst-5-en-9α-ol

To a solution of 3,3-ethylenedioxy-9α-hydroxyandrost-5-en-17-one (3.46 g) in nitromethane (75 ml) under a nitrogen atmosphere 1,2-diaminoethane (0.1 ml) was added at reflux temperature. After 24 hours of refluxing the reaction was almost complete as measured by TLC.

After cooling to room temperature the reaction mixture was concentrated under reduced pressure to give a solid, which was purified by column chromatography (silica gel; methylene chloride/diethyl ether 1/1) to provide the title compound.

Yield 3.50 g (90%).

NMR (CDCl$_3$): 0.938 (s,3H), 1.187 (s,3H), 2.55 (m,1H), 3.06 (m,2H), 3.94 (m,4H), 5.40 (m,1H), 6.89 (tr,1H).

IR (KBr): 3575 (OH), 1640 (C=C), 1510 (NO$_2$), 1345 (NO$_2$).

EXAMPLE 2

3,3-Ethylenedioxy-20-nitropregna-5,16-diene-9α,21-diol

Under a nitrogen atmosphere formaline (2 ml, 40% solution in water) and triethylamine (1 ml) were added to a stirred suspension of 3,3-ethylenedioxy-17-(nitromethylene)androst-5-en-9α-ol (0.50 g) in 2-propanol (10 ml). After stirring for one hour at room temperature the reaction was found to be complete as evidenced by TLC. The reaction mixture was poured into a mixture of water (200 ml) and acetic acid (3 ml) and stirred for 30 minutes. The resulting precipitate was filtered, washed with water and dried to afford 0.46 g of the title compound (85%). According to NMR the product was a 4:1 mixture of the two C20 diastereomers which were separated by chromotagraphy (silica gel; toluene/acetone 3/1) and analysed.

Diastereomer I: NMR (CDCl$_3$/DMSO-d6): 0.817 (s,3H), 1.183 (s, 3H), 3.78 (dd,1H), 3.93 (m,4H), 4.31 (dd,1H), 5.15 (dd,1H), 5.38 (m,1H), 5.98 (m,1H).

IR (KBr): 3537 (OH), 3410 (br OH), 1555 (NO$_2$).

Diastereomer II: NMR (CDCl3): 0.877 (s,3H), 1.194 (s,3H), 3.76 (dd,1H), 3.94 (m,4H), 4.23 (dd,1H), 5.10 (dd,1H), 5.39 (m, 1H), 5.95 (m,1H).

IR (KBr): 3538 (OH), 3400 (OH), 2557 (NO$_2$).

EXAMPLE 3

21-Acetoxy-3,3-ethylenedioxy-20-nitropregna-5,16-dien-9α-ol

Acetic anhydride (1.5 ml) was added to a stirred suspension of 3,3-ethylenedioxy-20-nitropregna-5,16-diene-9α,21-diol (1.00 g of diastereomer II, prepared according to example 2), and 4-dimethylaminopyridine (100 mg) in methylene chloride (10 ml) to give a clear solution. The reaction mixture was stirred for an additional 30 minutes and concentrated under reduced pressure. The residue was dissolved in methylene chloride and filtered over a silica gel column. The filtrate was evaporated under reduced pressure to afford a white solid which was dried under reduced pressure at 50° C.

Yield 0.92 g (84%) of the title compound.

NMR (CDCl$_3$): 0.869 (s,3H), 1.195 (s,3H), 2.05 (s,3H), 3.94 (m,4H), 4.37 (dd,1H), 4.54 (dd,1H), 5.20 (dd,1H), 5.39 (m,1H), 6.03 (m,1H).

IR (KBr): 3533 (OH), 1750 (CO), 1576 (NO$_2$).

EXAMPLE 4

The experiment of the previous example was repeated under the same conditions except that the starting compound was a mixture of the two C20 diastereomers. In the repeated experiment the title compound of example 3 was obtained as a mixture of the two C20 diastereomers. Yield 88%.

EXAMPLE 5

21-Acetoxy-9α-hydroxy-20-hydroxyiminopregna-4,16-dien-3-one

A filtered aqueous solution of chromous chloride, prepared from chromium (II) chloride (26.1 g), water (121.8 ml) concentrated hydrochloric acid (52.2 ml) and zinc powder (15.7 g) according to the method of J. R. Hanson and T. D. Organ; J. Chem. Soc.(C) 1970, 1182, was added under nitrogen to a stirred solution of 21-acetoxy-3,3-ethylenedioxy-20-nitropregna-5,16-dien-9α-ol (8.70 g as a mixture of 2 diastereomers) in acetone (1.3 l). After stirring for 45 seconds the reaction mixture was poured into an aqueous sodium chloride solution. The resulting layers were separated after which the aqueous layer was washed twice with diethyl ether (400 ml). The combined organic layers were washed once with aqueous sodium chloride solution (450 ml), dried and evaporated under reduced pressure to afford the title compound.

Yield 5.34 g (70%).

NMR (CDCl$_3$): 0.979 (s,3H), 1.344 (s,3H), 2.07 (s,3H), 2.42 (s,1H), 4.98 (s,2H), 5.89 (s,1H), 6.13 (m,1H), 8.63 (br s,1H).

IR (KBr): 3580 (OH), 1740 (CO), 1660 (CO).

EXAMPLE 6

21-Acetoxy-3,3-ethylenedioxy-20-hydroxyiminopregna-5,16-dien-9α-ol

In an additional experiment carried out as example 5 except that the reaction time was 30 seconds, a small amount of the intermediate compound 21-acetoxy-3,3-ethylenedioxy- 20-hydroxyiminopregna-5,16-dien-9α-ol was isolated by chromatography (silica gel, toluene/acetone 3/1).

NMR (CDCl$_3$): 0.947 (s,3H), 1.200 (s,3H), 2.07 (s,3H), 3.94 (m,4H), 4.93 (d, 1H), 4.99 (d, 1H), 5.39 (m,1H), 6.09 (m,1H) 9.01 (br s, 1H).

IR (KBr): 3360 (br OH), 1745 (CO).

EXAMPLE 7

21-Acetoxy-9α-hydroxypregna-4,16-diene-3,20-dione

A 15% (w/v) aqueous solution of titanium trichloride (4.1 ml) was added to a stirred suspension of 21-acetoxy-9α-hydroxy-20-hydroxyiminopregna-4,16-dien-3-one (0.50 g), ammonium acetate (1.5 g), acetic acid (10 ml) and acetone (3.75 ml) under nitrogen. After stirring at room temperature for 6 hours the reaction mixture was poured into water (30 ml) and extracted three times with diethyl ether. The combined organic layers were washed three times with 1N sodium hydroxide solution, then washed with aqueous sodium chloride solution and dried. The extract was evaporated under reduced pressure to afford the title compound as a foam.

Yield 0.35 g (73%).

NMR (CDCl$_3$): 0.972 (s,3H), 1.347 (s,3H), 2.17 (s,3H), 2.41 (s,1H), 4.88, 5.05 (2 x d,2H), 5.88 (s,1H), 6.79 (m,1H).

IR (KBr): 3500 (br OH), 1745 (CO), 1660 (CO).

EXAMPLE 8

21-Hydroxypregna-4,9(11),16-triene-3,20-dione

21-Acetoxy-9c-hydroxypregna-4,16-diene-3,20-dione (0.23 g) was added to a 70% (v/v) aqueous sulfuric acid solution (8 ml). After stirring at room temperature for 45 minutes, the reaction mixture was poured into ice water. The resulting precipitate was filtered, washed with water and dried to afford 0.14 g of the title compound (Yield 72%).

NMR (CDCl$_3$): 0.896 (s,3H), 1.352 (s,3H), 3.30 (tr,1H), 4.43 and 4.53 (2 x d,2H), 5.55 (d,1H), 5.74 (s,1H), 6.75 (tr,1H).

IR (KBr): 3437 (OH), 1670 (CO), 1660 (CO), 1609 (C=C), 1589 (C=C).

EXAMPLE 9

Ethyl (20Z)-20-formamido-9α-hydroxy-3-oxopregna-4,17(20)-dien-21-oate

Ethyl isocyanoacetate (1.64 g) in dry tetrahydrofuran (8 ml) was added slowly to a stirred suspension of potassium tert. butoxide (1.71 g) in dry tetrahydrofuran (60 ml) so that the temperature did not rise above 5° C. A solution of 3-methoxy-9α-hydroxyandrosta-3,5-dien-17-one (3.22 g) in dry tetrahydrofuran (15 ml) was added dropwise at 0° C. and the mixture was stirred at room temperature for 4 hours. Most of tetrahydrofuran was removed under reduced pressure and the product was taken up in cold water, adjusted to pH 0.8 with 4N aqueous hydrochloric acid and extracted with chloroform. The combined chloroform extracts were dried over anhydrous magnesium sulfate. The solvent was removed under reduced pressure and the product dried under vacuum. Yield 3.55 g. NMR spectra showed predominantly the formation of the title compound together with small amounts of ethyl (20E)-20-formamido-9α-hydroxy-3-oxopregna-4,17(20)-dien-21-oate and tert. butyl (20Z)-20-formamide-9α-hydroxy-3-oxopregna-4,17(20)-dien-21-oate. The compounds were isolated through chromatography and separately identified through spectral data.

Ethyl (20Z)-20-formamido-9α-hydroxy-3-oxopregna-4,17(20)-dien-21-oate

NMR (CDCl$_3$): 0.969 and 0.987 (2 x s,3H), 1.26 and 1.29 (2×tr, 3H), 1.316 and 1.322 (2 x s,3H), 2.40 (s,1H), 4.19 (2× q,2H), 5.85 (s,1H), 7.03 and 7.24 (d and s,1H), 7.92 and 8.20 (d and s,1H).

IR (KBr): 3400 (br, OH and NH), 1650 (CO).

Ethyl (20E)-20-formamido-9α-hydroxy-3-oxopregna-4,17(20)-dien-21-oate

NMR (CDCl$_3$): 1.101 (s,3H), 1.29 (tr,3H), 1.322 (s,3H), 2.39 (s,1H), 4.19 (2×q,2H), 5.83 (s,1H), 7.63 (s,1H), 8.09 (s,1H).

IR (KBr): 3400 (br, OH and NH), 1680 (CO).

Tert. butyl (20Z)-20-formamido-9α-hydroxy-3-oxopregna-4,17(20)-dien-21-oate

NMR (CDCl$_3$): 0.979 and 0.984 (2×s,3H), 1.321 and 1.326 (2×s,3H), 1.48 and 1.49 (2×s,9H), 2.41 (s,1H), 5.88 (s,1H), 6.59 and 6.71 (d and s,1H), 7.94 and 8.21 (d and s,1H).

IR (KBr): 3400 (br, OH and NH), 1650 (CO).

Double signals in the NMR spectra of the (20Z) compounds are caused by the two rotamer forms of the 20-formamido group.

EXAMPLE 10

Ethyl (20Z)-20-formamido-9α-hydroxy-3-methoxypregna-3,5,17(20)-trien-21-oate Potassium tert. butoxide (1.71 g) was added to dry tetrahydrofuran (60 ml) under nitrogen. The solution was cooled to 0° C. and a solution of ethyl isocyanoacetate (1.64 g) in tetrahydrofuran (10 ml) was added dropwise, while keeping the temperature below 0° C. Next, a solution of 9α-hydroxy-3-methoxyandrosta-3,5-dien-17-one (3.21 g) in tetrahydrofuran (60 ml) was added. After stirring for 5 hours at room temperature the mixture was poured into 400 ml of saturated aqueous ammonium chloride solution and extracted twice with ethyl acetate. The combined organic layers were washed three times with water, dried (MgSO$_4$) and concentrated under reduced pressure. The crude product (3.20 g) was purified by chromatography (silica gel, toluene/acetone 4/1 containing 0.1% triethylamine) to provide 0.99 g of the title compound. NMR spectra showed the formation of the Z-isomer of the title compound as a mixture of the two rotamer forms of the 20-formamido group.

NMR (CDCl$_3$): 0.963 and 0.965 (2×s, 3H), 1.084 (s, 3H), 1.26 (tr, 3H), 3.56 (s, 3H), 4.19 (m, 2H), 5.16 (s, 1H), 5.29 (m, 1H), 6.58 and 6.81 (d and s, 1H), 7.94 and 8.22 (d and s, 1H).

IR (KBr): 3400 (br, OH and NH), 1670 (CO).

EXAMPLE 11

(20Z)-20-Formamido-3-methoxypregna-3,5,17(20)-triene-9α,21-diol

Under a nitrogen atmosphere sodium borohydride (0.53 g) and lithium aluminium hydride (0.65 g) were added to a stirred solution of ethyl (20Z)-20-formamido-9α-hydroxy-3-methoxypregna-3,5,17(20)-trien-21-oate (4.85 g, prepared according to example 10), in dry tetrahydrofuran (100 ml) at 0° C. The reaction mixture was stirred at 5° C. for 2 hours, after which another 0.54 g of sodium borohydride and 0.65 g of lithium aluminium hydride were added. Stirring was continued at 5° C. for 1.5 hours, then ethanol (50 ml) was added dropwise to decompose excess reducing agent. After adding 60 ml of an aqueous solution of sodium potassium tartrate, the reaction mixture was filtered and extracted with ethyl acetate. The organic phase was washed with an aqueous sodium carbonate solution and with water, dried (MgSO$_4$) and concentrated under reduced pressure. The residue (3.02 g) was purified by column chromatography (toluene/acetone 2/1 containing 0,1% triethylamine) to provide 1.08 g of the title compound.

NMR (CDCl$_3$): 0.929 (s, 3H), 1.092 (s, 3H), 3.56 (s, 3H), 4.13 (ABq, 2H), 5.16 (s, 1H), 5.29 (m, 1H), 7.15 (s, 1H), 8.11 (s, 1H).

IR (KBr): 3400 (br, OH and NH), 1650 (CO).

EXAMPLE 12

9α,21-Dihydroxypregn-4-ene-3,20-dione

Aqueous 5N hydrochloric acid (1 ml) was added to a stirred solution of (20Z)-20-formamido-3-methoxypregna-3,5,17(20)-triene-9α,21-diol (70 mg) in methanol (4 ml). The reaction mixture was stirred at room temperature for 1 hour, then extracted with ethyl acetate. The organic extract was washed with an aqueous sodium bicarbonate solution, twice with water, dried and concentrated under reduced pressure to afford the title compound.

NMR (CDCl₃): 0.700 (s, 3H), 1.315 (s, 3H), 4.02 (m, 2H), 5.88 (s, 1H).

IR (KBr): 3400 (br, 2×OH), 1695 (CO), 1635 (CO).

EXAMPLE 13

Ethyl (20Z)-3,3-ethylenedioxy-20-formamido-9α-hydroxy-16β-methylpregna-5,17(20)-dien-21-oate Under a nitrogen atmosphere a solution of ethyl isocyanoacetate (1.70 g) in dry tetrahydrofuran (10 ml) was added dropwise to a stirred solution of potassium tert. butoxide (1.70 g) in dry tetrahydrofuran (20 ml) at 5° C. over 10 minutes. After stirring for 10 minutes a solution of 3,3-ethylenedioxy-9α-hydroxy-16β-methylandrost-5-en-17-one (3.60 g) in dry tetrahydrofuran (40 ml) was added dropwise at 10° C. over 5 minutes. The reaction mixture was stirred at room temperature for 20 hours. To complete the reaction the same quantities of ethyl isocyanoacetate (in 10 ml of tetrahydrofuran) and potassium tert. butoxide (in 20 ml of tetrahydrofuran) were added dropwise and stirring was continued at room temperature for 2 hours. The reaction mixture was poured into water (100 ml) and extracted twice with diethyl ether. The combined organic layers were washed with water, dried and concentrated under reduced pressure to afford 5.4 g of a foam. Purification by chromatography (silica gel, toluene/acetone 1/1) provided the title compound as a mixture of 2 rotamers.

NMR (CDCl₃): 0.936 and 0.946 (2×s, 3H), 1.079 and 1.143 (2×d, 3H), 1.155 (s, 3H), 1.289 and 1.299 (2 x t, 3H), 3.93 (m, 4H), 4.21 (q, 2H), 5.39 (t, 1H), 6.61 and 6.90 (d and s, 1H), 7.93 and 8.17 (d and s, 1H).

IR (KBr): 3300 (br, OH, NH), 1710 (CO), 1692 (CO).

EXAMPLE 14

(20Z)-3,3-Ethylenedioxy-20-formamido-16β-methylpregna-5,17(20)-diene-9α,21-diol

Under a nitrogen atmosphere lithium aluminium hydride (125 mg) was added to a stirred solution of ethyl (20Z)-3,3-ethylenedioxy-20-formamido-9α-hydroxy-16β-methylpregna-5,17(20)-dien-21-oate (0.50 g, prepared according to example in dry tetrahydrofuran (10 ml) at room temperature. After stirring at room temperature for 1 hour TLC indicated the reaction to be complete. A few drops of water were added carefully to the stirred reaction mixture followed by more water and diethyl ether. The heterogeneous mixture was filtered over dicalite and the residue was washed with diethyl ether. The organic layer of the filtrate was separated and washed with water to neutral pH, dried and concentrated under reduced pressure to afford 0.20 g of a foam which was purified by chromatography (silica gel, toluene/acetone 1/1) thus providing 0.12 g of the title compound as a mixture of 2 rotamers.

NMR (CDCl₃): 0.884 and 0.899 (2×s, 3H), 1.146 (s, 3H), 1.20 (d, 3H), 3.94 (m, 4H), 4.18 (m, 2H), 5.36 (m, 1H) 7.12 and 7.31 (d and s, 1H), 8.12 and 8.15 (d and s, 1H).

IR (KBr): 3425 (br, NH, OH), 1683 (CO), 1663 (C=C).

EXAMPLE 15

21-Acetoxy-3,3-ethylenedioxy-20-formamido-16β-methylpregna-5,17(20)-dien-9α-ol

A solution of 3,3-ethylenedioxy-20-formamido-16β-methylpregna-5,17(20)-diene-9α,21-diol (80 mg) in pyridine (0.25 ml) and acetic anhydride (0.12 ml) was stirred at room temperature for 7 hours after which TLC indicated the conversion to be complete. Methylene chloride and water were added to the reaction mixture. The organic phase was washed with water to neutral pH, dried and concentrated under reduced pressure to afford 50 mg of the title compound as a mixture of the two rotamer forms of the 20-formamido group.

NMR (CDCl₃) 0.910 and 0.921 (2×s, 3H), 1.120 (d, 3H), 1.155 (s, 3H), 2.04 and 2.07 (2×s, 3H), 3.93 (m, 4H), 4.60 and 4.68, 4.72 and 4.88 (2×2 d, 2H), 5.38 (s, 1H), 6.84 and 6.94 (d and s, 1H), 806 and 8.14 (d and s, 1H).

IR (KBr): 3250 (br OH), 1745 (CO), 1690 (CO), 1660 (C=C).

EXAMPLE 16

9α,21-Dihydroxy-16β-methylpregn-4-ene-3,20-dione

Aqueous 5N hydrochloric acid (1 ml) was added to a solution of (20Z)-3,3-ethylenedioxy-20-formamido-16β-methylpregna-5,17(20)-diene-9α,21-diol (100 mg, prepared according to example 15) in methanol (4 ml). The reaction mixture was stirred at room temperature for 1 hour, after which TLC indicated the hydrolysis to be complete. Methylene chloride (10 ml) and water (10 ml) were added, and the heterogeneous mixture was concentrated under reduced pressure. The residue was dissolved in a mixture of methylene chloride and water. The layers were separated and the organic layer was washed with water to neutral pH, dried and concentrated under reduced pressure to afford 20 mg of the title compound. A crystalline solid, formed in the combined aqueous layers, was filtered, washed with water and dried to afford another 0 mg of the title compound.

NMR (CDCl₃): 0.732 (s, 3H), 0.992 (d, 3H), 1.316 (s, 3H), 4.12 and 4.21 (2×d, 2H), 5.87 (s, 1H).

IR (KBr): 3460 (OH), 3400 (OH), 1703 (CO), 1646 (CO).

EXAMPLE 17

Ethyl (20Z)-20-formamido-9o-hydroxy-3-methoxy-16-methylpregna-3,5,17(20)-trien-21-oate Under nitrogen a solution of ethyl isocyanoacetate (1.70 g) in dry tetrahydrofuran (10 ml) was added dropwise to a stirred solution of potassium tert. butoxide (1.70 g) in dry tetrahydrofuran (20 ml) at 5° C. over 15 minutes. After stirring for 10 minutes a solution of 9α-hydroxy-3-methoxy-16α-methylandrosta-3,5-dien-17-one (1.70 g) in dry tetrahydrofuran (20 ml) was added dropwise at 5° C. over 5 minutes. Stirring was continued at room temperature for 2.5 hours, then the reaction mixture was poured into water (100 ml) and extracted twice with diethyl ether. The combined organic layers were washed with water, dried and concentrated under reduced pressure to afford 1.53 g of a light yellow foam. Chromatography (silica gel, toluene/acetone 3/1 containing 0.1% triethylamine) provided 0.26 g of the title compound as a mixture of 2 rotamers. The stereochemistry on C16 has not been ascertained.

NMR (CDCl$_3$): 0.950 and 0.965 (2×s, 3H), 1.091 (s, 3H), 1.153 (d, 3H), 1.29 and 1.30 (2×t, 3H), 3.57 (s, 3H), 4.21 (m, 2H), 5.17 (br, s, 1H), 5.29 (t, 1H), 6.66 and 6.93 (d and s, 1H), 7.91 and 8.18 (d and s, 1H).

IR (KBr): 3400 (br, NH and OH), 1700 (CO), 1690 (CO).

EXAMPLE 18

Ethyl (20E)-20-chloro-3,3-ethylenedioxy-9α-hydroxypregna-5,17(20)-dien-21-oate

Under a nitrogen atmosphere a suspension of freshly activated zinc dust (8.52 g) in dry tetrahydrofuran (250 ml) was stirred at −10° C. for 15 minutes followed by the addition of diethylaluminium chloride (60 ml of a 1M solution in hexane). Stirring was continued for 10 minutes after which a solution of ethyl trichloroacetate (11.48 g) in dry tetrahydrofuran (50 ml) was added dropwise over 30 minutes while keeping the temperature below 0° C. The mixture was stirred for 15 minutes after which a solution of 3,3-ethylenedioxy-9α-hydroxyandrost-5-en-17-one (10.73 g) in dry tetrahydrofuran (200 ml) was added dropwise over a period of 135 minutes while keeping the temperature below −10° C. Stirring was continued at −10° C. for 2 hours. Next, aqueous 1N hydrochloric acid (350 ml) and diethyl ether (200 ml) were added. The heterogeneous mixture was filtered over dicalite and the residue was washed with diethyl ether. The filtrate was transferred into a separatory funnel and allowed to settle. The organic layer was washed with water to neutral pH, dried (MgSO$_4$) and concentrated under reduced pressure to afford 14.63 g of an oily residue. Chromatography (silica gel, toluene/acetone 6/1) provided 3.07 g of the title compound as a single isomer.

NMR (CDCl$_3$): 1.033 (s, 3H), 1.162 (s, 3H), 1.323 (t, 3H), 3.93 (m, 4H), 4.24 (m, 2H), 5.38 (m, 1H).

IR (KBr): 3570 (OH), 1712 (CO).

EXAMPLE 19

Methyl (20Z)-3,3-ethylenedioxy-9α-hydroxy-20-methoxypregna-5,17(20)-dien-21-oate To a solution of sodium (171 mg) in anhydrous methanol (10 ml) was added ethyl (20E)-20-chloro-3,3-ethylenedioxy-9α-hydroxypregna-5,17(20)-dien-21-oate (306 mg, as prepared in example 18), after which the reaction mixture was refluxed under nitrogen for 21 hours. The reaction mixture was cooled to room temperature. After adding methanol (20 ml) and water (10 ml) the mixture was neutralised with aqueous 5N hydrochloric acid. More water (30 ml) was added and a precipitate was formed. The solid was filtered, washed with water and dried to afford 46 mg of the title compound as a single isomer.

NMR (CDCl$_3$): 0.941 (s, 3H), 1.177 (s, 3H), 3.55 (s, 3H), 3.77 (s, 3H), 3.94 (m, 4H), 5.39 (m, 1H).

IR (KBr): 3580 (OH), 1715 (CO).

EXAMPLE 20

(20Z)-3,3-Ethylenedioxy-20-methoxypregna-5,17(20)-diene-9α,21-diol

Under nitrogen a 1M solution of diisobutylaluminium hydride in toluene (0.1 ml) was added to a stirred solution of methyl (20Z)-3,3-ethylenedioxy-9α-hydroxy-20-methoxypregna-5,17(20)-dien-21-oate (112 mg, prepared according to Example 19) in dry toluene (8 ml) at −20° C. The reaction mixture was stirred at −20° C. for 30 minutes. To complete the reaction the same quantity of diisobutylaluminium hydride solution was added and stirring was continued at −20° C. for 5 minutes. Next, water (2 ml) was added and the mixture was stirred at 0° C. for 1 hour. The heterogeneous mixture was filtered, then the filtrate was concentrated under reduced pressure to afford 66 mg of the title compound as a white solid.

NMR (CDCl$_3$) 0.896 (s, 3H), 1.167 (s, 3H), 3.52 (s, 3H), 3.93 (m, 4H), 4.08 and 4.19 (2×d, 1H), 5.38 (m, 1H).

IR (KBr): 3420 (br, 2×OH), 1665 (C=C).

EXAMPLE 21

9α,21-Dihydroxypregn-4-ene-3,20-dione (20Z)-3,3-Ethylenedioxy-20-methoxypregna-5,17(20)-diene-21-diol (22 mg) was dissolved in 3 ml of a solution prepared by the addition of 8 drops of 70% aqueous perchloric acid to a mixture of methanol (19) and water (10 ml). After stirring at room temperature overnight a few drops of aqueous sodium bicarbonate solution were added. Then, methanol was evaporated under reduced pressure and the residue was extracted with methylene chloride (20 ml) and water (5 ml). The organic layer was dried and concentrated under reduced pressure to afford 13 mg of the title compound. IR and NMR were identical with the spectra of the product obtained in Example 12.

EXAMPLE 22

Ethyl (20E)-20-chloro-3,3-ethylenedioxy-9α-hydroxy-16β-methylpregna-5,17(20)-dien-21-oate Using the procedure of Example 18, 3,3-ethylenedioxy-9α-hydroxy-16β-methylandrost-5-en-17-one (3.60 g) was reacted with ethyl trichloroacetate (2.78 ml) in the presence of zinc dust (2.83 g) and diethylaluminium chloride (20 ml, 1M in hexane). Chromatography (silica gel, toluene/acetone 3/1) of the crude product (3.0 g) afforded the title compound as a single isomer.

NMR (CDCl$_3$): 0.902 (s, 3H), 1.01 (d, 3H), 1.155 (s, 3H), 1.31 (t, 3H), 3.93 (m, 4H), 4.25 (q, 2H), 5.37 (m, 1H).

IR (KBr): 3525 (br, OH), 1728 (CO).

EXAMPLE 23

Methyl (20E)-3,3-ethylenedioxy-go-hydroxy-20-methoxypregna-5,17(20)-dien-21-oate Under a nitrogen atmosphere a solution of 3,3-ethylenedioxy-9α-hydroxy-androst-5-en-17-one (1.78 g) and methyl methoxydichloroacetate (1.73 g) in dry tetrahydrofuran (30 ml) was added dropwise to a stirred suspension of freshly activated zinc dust (1.85 g) and diethylaluminium chloride (11 ml of a 1M solution in hexane) in dry tetrahydrofuran (20 ml) at 10° C. over a period of 30 minutes. The resulting suspension was stirred at 0° C. for 20 minutes, then at room temperature for 1 hour. The suspension was cooled to 0° C. and filtered. The cold filtrate was added dropwise to a mixture of pyridine/water (4/1; 50 ml). The resulting mixture was extracted three times with methylene chloride. The combined diluted acetic acid, aqueous sodium bicarbonate solution and water. The methylene chloride extract was dried and concentrated under reduced pressure. The crude product (2.07 g) was chromatographed (silica gel, toluene/acetone 3/1) to provide the title compound.

NMR (CDCl$_3$): 1.016 (s, 3H), 1.175 (s, 3H), 3.52 (s, 3H), 3.78 (s, 3H), 3.94 (m, 4H), 5.39 (m, 1H).

EXAMPLE 24

3,3-Ethylenedioxypregna-5,17(20)-dien-9α-ol

A mixture of sodium hydride (2.42 g) in dimethylsulfoxide (150 ml) was heated under nitrogen for 45 minutes while stirring. After cooling to room temperature a solution of ethyltriphenylphosphonium iodide (42.3 g; prepared according to J.Org. Chem. 1966, 31, 24) in dimethylsulfoxide (150 ml) was added rapidly. After stirring for 5 minutes a solution of 3,3-ethylenedioxy-9α-hydroxyandrost-5-en-17-one (7.0 g) in dimethylsulfoxide (150 ml) was added dropwise over 10 minutes. The reaction mixture was stirred at 70° C. for 10 minutes, then at room temperature for 16 hours. Stirring was continued at 60° C. for 8 hours after which the reaction mixture was poured into ice water. After three extractions with diethyl ether, the combined organic layers were washed with water, dried and concentrated under reduced pressure. The residue (9.81 g) was purified by chromatography (Al$_2$O$_3$; toluene/acetone 3/1 containing 0.1% triethylamine) to afford 2.29 g of the title compound, as a 9:1 mixture of Z and E diastereoisomers.

NMR (CDCl$_3$) 0.743 and 0.889 (2×s, 3H), 1.166 (s, 3H), 1.65 (d, 3H), 3.93 (br. s, 4H), 5.13 (m, 1H), 5.39 (br, s, 1H).

EXAMPLE 25

3,20-Dihydroxyiminopregna-4,16-dien-9α-ol

Nitrosyl chloride, prepared from sodium chloride and nitrosyl sulfuric acid, was passed into methylene chloride (7 ml) at 0° C., until a burgundy colour had developed. The solution was added in one action to 3,3-ethylenedioxypregna-5,17(20)-dien-9α-ol (301 mg). The reaction mixture was stirred for 3 minutes after which the solvents were evaporated under reduced pressure. The residue was taken up in a mixture of tetrahydrofuran (15 ml) and water (1.5 ml). Triethylamine (1.6 ml) was added dropwise, then the mixture was refluxed for 2 hours. After cooling to room temperature, methylene chloride (100 ml) was added and the mixture was washed twice with a 5% aqueous potassium carbonate solution, dried (MgSO$_4$) and concentrated under reduced pressure. The crude product (251 mg) was chromatographed (silica gel, toluene/acetone 3/1) to afford the title compound as a isomeric mixture of syn and anti 20-oximes, both containing a 3-hydroxyimino group in the syn configuration.

NMR (CDCl$_3$): 0.956 (s, 3H), 1.245 (s, 3H), 1.97 (s, 3H), 6.03 (br, s, 1H), 6.44 (s, 1H), 9.0 (br, s, 1H).

EXAMPLE 26

3,3-Ethylenedioxy-16α-methylpregna-5,17(20)-dien-9α-ol

Under a nitrogen atmosphere ethyltriphenylphosphonium iodide (4.2 g) was added to a stirred solution of potassium tert. butoxide (1.12 g) in dry tetrahydrofuran (15 ml) at room temperature. The resulting orange suspension was stirred for 30 minutes after which a solution of 3,3-ethylenedioxy-9α-hydroxy-16β-methylandrost-5-en-17-one (1.0 g) in dry tetrahydrofuran was added dropwise. The reaction mixture was stirred at 50° C. for 1 hour, then at reflux temperature for 5 hours. After additional stirring overnight at room temperature, the mixture was poured into water and extracted with ethyl acetate. The organic layer was washed with water, dried and concentrated under reduced pressure to afford 3.1 g of a solid. Chromatography (silica gel, hexane/diethyl ether 1/1 followed by elution with toluene/acetone 2/1) afforded 0.50 g of the title compound.

NMR (CDCl$_3$): 0.900 (s, 3H), 1.034 (d, 3H), 1.167 (s, 3H), 1.675 and 1.679 (2×d, 3H), 3.93 (m, 4H), 5.13 (m, 1H), 5.38 (m, 1H).

IR (KBr): 3575 (OH).

EXAMPLE 27

20-Isocyano-3,3-ethylenedioxypregna-5,17(20)-dien-9α-ol

Under a nitrogen atmosphere potassium tert. butoxide (2.80 g) was added to a stirred solution of 3,3-ethylenedioxy-9α-hydroxyandrost-5-en-17-one (3.70 g) in dry tetrahydrofuran (75 ml) at 0° C. After stirring at this temperature for 10 minutes a solution of diethyl α-isocyanoethylphosphonate (8.09 g) in dry tetrahydrofuran (20 ml) was added dropwise over 45 minutes, while keeping the temperature below 3° C. The reaction mixture was stirred at 3° C. for 5 hours. Stirring was continued at room temperature for 40 hours, then the reaction mixture was poured into a mixture of water (300 ml) and saturated sodium chloride solution (225 ml) and extracted twice with diethyl ether. The combined organic layers were dried (MgSO$_4$) and concentrated under reduced pressure. The residue was chromatographed (silica gel, toluene/acetone 5/1) to obtain the title compound (2.86 g) as a mixture of 2 diastereomers.

NMR (CDCl$_3$): 0.896 and 0.931 (2×s, 3H), 1.170 (s, 3H), 1.84 1.95 (2×s, 3H), 3.93 (m, 4H), 5.38 (m, 1H).

IR (KBr): 3559, 3585 (OH), 2108 (NC).

EXAMPLE 28

9α-Hydroxypregn-4-ene-3,20-dione

A solution of 20-isocyano-3,3-ethylenedioxypregna-5,17(20)-dien-9α-ol (2.30 g) in a mixture of tetrahydrofuran (60 ml) and aqueous 2N hydrochloric acid (20 ml) was refluxed for 1 hour. The reaction mixture was cooled to room temperature after which water (25 ml) and diethyl ether (100 ml) were added. The mixture was neutralised with 1N sodium hydroxide solution. After separating the layers the aqueous phase was extracted twice with diethyl ether (50 ml). The combined organic layers were dried (MgSO$_4$) and concentrated under reduced pressure to afford 2.02 g of the title compound.

NMR (CDCl$_3$): 0.675 (s, 3H), 1.322 (s, 3H), 2.12 (s, 3H), 5.85 (s, 1H).

IR (KBr): 3375 (OH), 1700 (CO), 1635 (CO).

EXAMPLE 29

Pregna-4,9(11)-diene-3,20-dione

A solution of 9α-hydroxypregn-4-ene-3,20-dione (218 mg) in 70% (v/v) aqueous sulfuric acid was stirred at room temperature for 1 hour after which the reaction mixture was added dropwise to a stirred mixture of water (5 ml) and ethyl acetate (5 ml). The organic layer was washed with a 5% aqueous potassium carbonate solution, then with water to neutral pH, dried (MgSO$_4$) and concentrated under reduced pressure. The crude product (149 mg), still containing some starting material, was purified by chromatography (silica gel, toluene/acetone 3/1) to afford the title compound.

NMR (CDCl$_3$): 0.617 (s, 3H), 1.338 (s, 3H), 2.14 (s, 3H), 5.53 (m, 1H), 5.74 (s, 1H).

IR (KBr): 1705 (CO), 1678 (CO).

EXAMPLE 30

20-Isocyano-3-methoxypregna-3,5,17(20)-trien-9α-ol

Using the procedure of Example 27, 3.10 g of 9α-hydroxy-3-methoxyandrosta-3,5-dien-17-one and 8.02 g of diethyl α-isocyanoethylphosphonate were reacted for 5 hours to produce 2.39 g of the title compound as a mixture of 2 diastereomers. Chromatography was performed on silica gel with toluene/acetone 9/1 containing 0,1% triethylamine as eluent.

NMR (CDCl$_3$): 0.915 and 0.950 (2×s, 3H), 1.097 and 1.104 (2×s, 3H), 1.848 and 1.956 (2×s, 3H), 3.57 (s, 3H), 5.16 (s, 1H), 5.29 (m, 1H).

IR (KBr): 3460 (br, OH), 2240 and 2105 (NC), 1655 (C=C).

EXAMPLE 31

9α,17α-Dihydroxypregn-4-ene-3,20-dione

Under nitrogen a mixture of formic acid (70 mg) and dry methylene chloride (16 ml) was added to a stirred solution of 20-isocyano-3-methoxypregna-3,5,17(20)-trien-9α-ol (186 mg) in dry methylene chloride (4 ml) over a period of 15 minutes and the reaction mixture was stirred overnight. Next, metachloroperbenzoic acid was added in one portion at 0° C. and the mixture was stirred at 0° C. for 20 minutes, followed by the addition of dimethyl sulfide (0.2 ml), acetic acid (16 ml) and water (6 ml). The mixture was heated at 60° C. for 1.5 hours, then, after the addition of toluene (15 ml) concentrated under reduced pressure. The residue was taken up in ethanol (15 ml) and aqueous 0.5N sodium hydroxide (8 ml) and the mixture was stirred at 60° C. for 15 minutes. Next, the mixture was cooled to room temperature and extracted three times with methylene chloride (20 ml). The combined organic layers were dried (MgSO$_4$) and concentrated under reduced pressure to afford 146 mg of a solid. Chromatography (silica gel, toluene/acetone 2/1) afforded the title compound.

NMR (CDCl$_3$): 0.743 (s, 3H), 1.318 (s, 3H), 2.27 (s, 3H), 5.86 (s, 1H).

IR (KBr): 3485 (2×OH), 1700 (CO), 1665 (CO), 1614 (C=C).

EXAMPLE 32

21-Bromo-17α-formyloxy-9α-hydroxypregn-4-ene-3,20-dione

Under nitrogen a mixture of formic acid (4 ml) and ethyl acetate (20 ml) was added dropwise to a stirred solution of 20-isocyano-3-methoxypregn-3,5,17(20)-trien-9α-ol (202 mg) in ethyl acetate (20 ml) and the reaction mixture was stirred at room temperature overnight. Then, the mixture was washed with aqueous 5% potassium carbonate, dried and concentrated under reduced pressure. Without further purification the residue was dissolved in methylene chloride (40 ml). After the addition of meta-chloroperbenzoic acid (255 mg) at 0° C., the solution was stirred for 25 minutes. Next, 16 drops of dimethyl sulfide were added to destroy excess meta-chloroperbenzoic acid and the solution was stirred for 30 minutes. Toluene (80 ml) was added and the mixture was heated until 60 ml of the toluene had destilled. Then, the mixture was cooled to room temperature and dry pyridine (2 ml) was added, followed after 10 minutes by a solution of pyridinium bromide perbromide (240 mg) in methylene chloride (20 ml). The reaction mixture was stirred at room temperature for 10 minutes, then acetic acid (12 ml) and a solution of sodium metabisulfite (100 mg) in water (4 ml) were added. After stirring at about 65° C. for 1 hour the solvents were evaporated and the residue was taken up in methylene chloride/diethyl ether 2/1 (80 ml) and washed successively with water, aqueous 5% sodium bicarbonate solution and aqueous saturated sodium chloride solution, dried (MgSO$_4$) and concentrated under reduced pressure to afford 136 mg of a solid which was purified by chromatography (silica gel, toluene/acetone 5/1) to afford the title compound.

NMR (CDCl$_3$): 0.758 (s, 3H), 1.337 (s, 3H), 2.42 (s, 1H), 3.98 and 4.07 (2×d, 2H), 5.89 (s, 1H), 8.09 (s, 1H).

IR (KBr): 3400 (OH), 1720 (CO), 1636 (CO).

EXAMPLE 33

Ethyl 20-cyano-3,3-ethylenedioxy-9α-hydroxypregna-5,17(20)-dien-21-oate

A solution of 3,3-ethylenedioxy-9α-hydroxyandrost-5-en-17-one (1.73 g), ethyl cyanoacetate (5.32 ml) and potassium fluoride (4.35 g) in ethanol (30 ml) was stirred in a sealed bottle at 120° C. for 66 hours. According to TLC most of the starting material was converted. The reaction was concentrated under reduced pressure after which the residue was dissolved in methylene chloride (100 ml). The extract was washed three times with aqueous saturated sodium bicarbonate, then twice with water. The methylene chloride extract was dried, then concentrated under reduced pressure to afford 2.46 g of crude product, which was purified by chromatography (silica gel, toluene/acetone 9/1). Yield 1.78 g of the title compound.

NMR (CDCl$_3$): 1.028 (s, 3H), 1.182 (s, 3H), 1.32 (m, 3H), 3.94 (m, 4H), 4.24 (m, 2H), 5.39 (m, 1H).

IR (KBr): 2200 (CN), 1725 (CO), 1675 (C=C), 1625 (C=C).

EXAMPLE 34

Ethyl 20-cyano-3,3-ethylenedioxy-9α-hydroxypregn-5-en-21-oate

Sodium borohydride (0.70 g) was added in small portions to a stirred solution of ethyl 20-cyano-3,3-ethylenedioxy-9α-hydroxypregna-5,17(20)-dien-21-oate (1.76 g) in dry tetrahydrofuran (15 ml). After stirring at room temperature for 5 hours, lithium aluminium hydride (0.12 g) was added in 3 portions and stirring was continued for 3 hours. Aqueous saturated potassium dihydrogen phosphate (15 ml) was added and the mixture was extracted with ethyl acetate. The organic extract was washed with aqueous sodium bicarbonate, then washed twice with water, dried and concentrated under reduced pressure to afford 0.82 g of the title compound.

NMR (CDCl$_3$): 0.781 (s, 3H), 1.164 (s, 3H), 1.31 (m, 3H), 3.93 (m, 4H), 4.22 (m, 2H), 5.37 (m, 1H).

IR (KBr): 2220 (CN), 1750 (CO).

CHART A
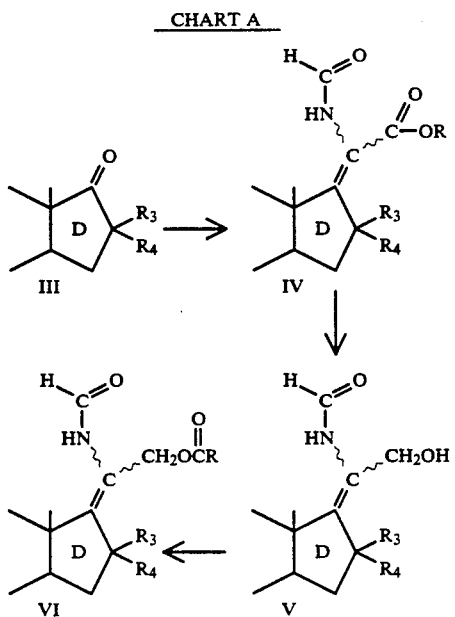
R₃ = H, R₄ = H, OH, CH₃ or
R₃ + R₄ = methylene
R = (1-6C)alkyl
CHART B
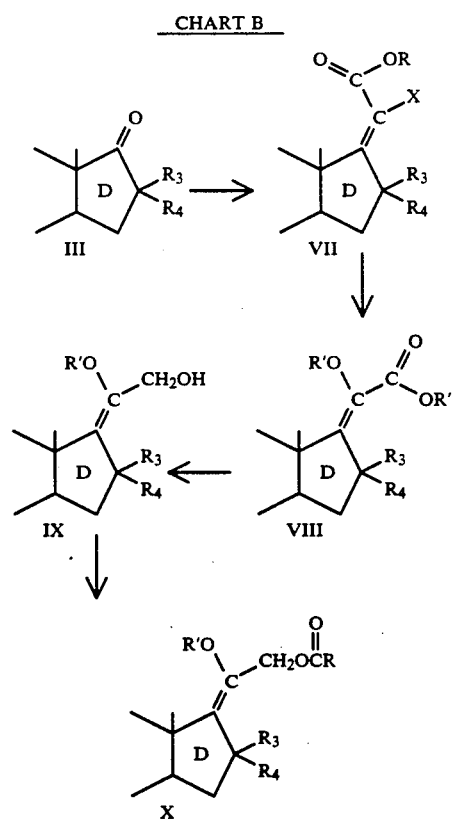
R and R' are the same or different (1-6C)alkyl
X = halogen
R₃ = H, R₄ = H, OH, CH₃ or
R₃ + R₄ = methylene
CHART C
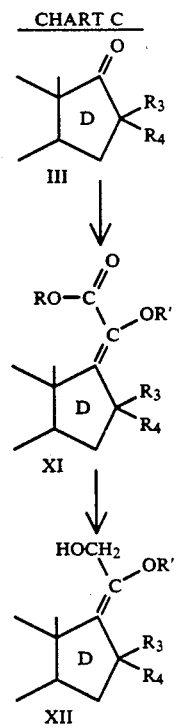
R and R' are the same or different (1-6C)alkyl
R₃ = H, R₄ = H, OH, CH₃ or
R₃ + R₄ = methylene
CHART D
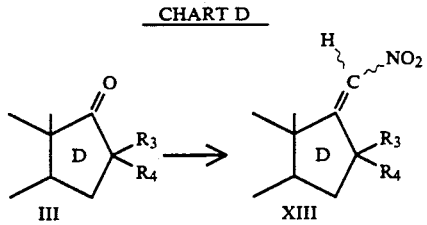
CHART E
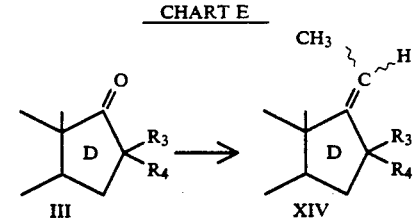
R₃ = H, R₄ = H, OH, CH₃ or
R₃ + R₄ = methylene
CHART F
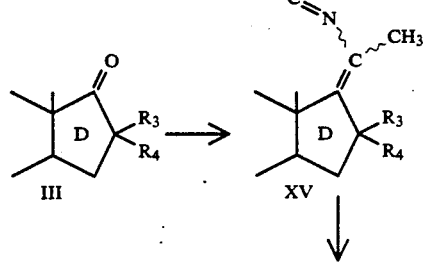

CHART F -continued
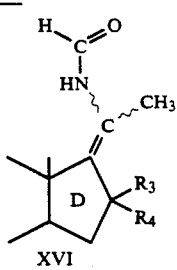
R₃ = H, R₄ = H, OH, CH₃ or
R₃ + R₄ = methylene
R = (1-6C)alkyl
CHART G
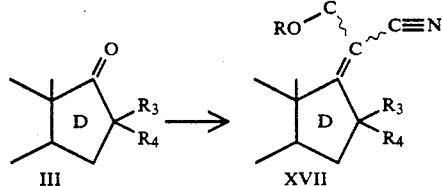
CHART H
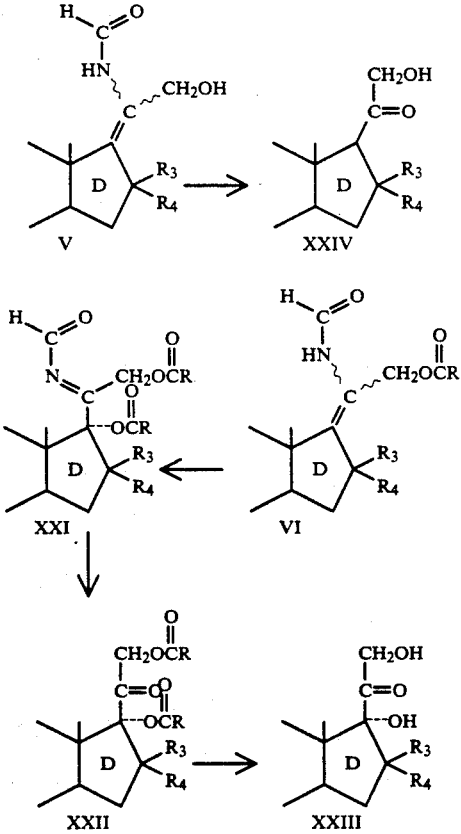
R₃ = H, R₄ = H, OH, CH₃ or
R₃ + R₄ = methylene
R = (1-6C)alkyl
R and R' are the same or different (1-6C)alkyl
CHART I
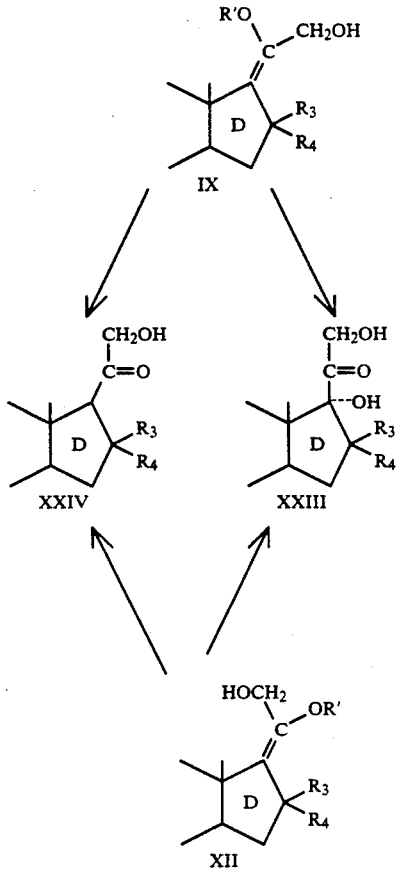
R₃ = H, R₄ = H, OH, CH₃ or
R₃ + R₄ = methylene
R' = (1-6C)alkyl
CHART J
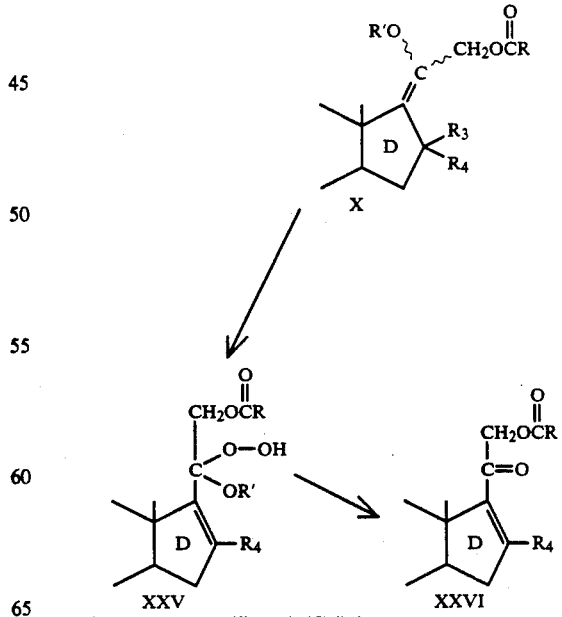
R and R' are the same or different (1-6C)alkyl
R₃ = H, R₄ = H, OH, CH₃ or
R₃ + R₄ = methylene CHART K
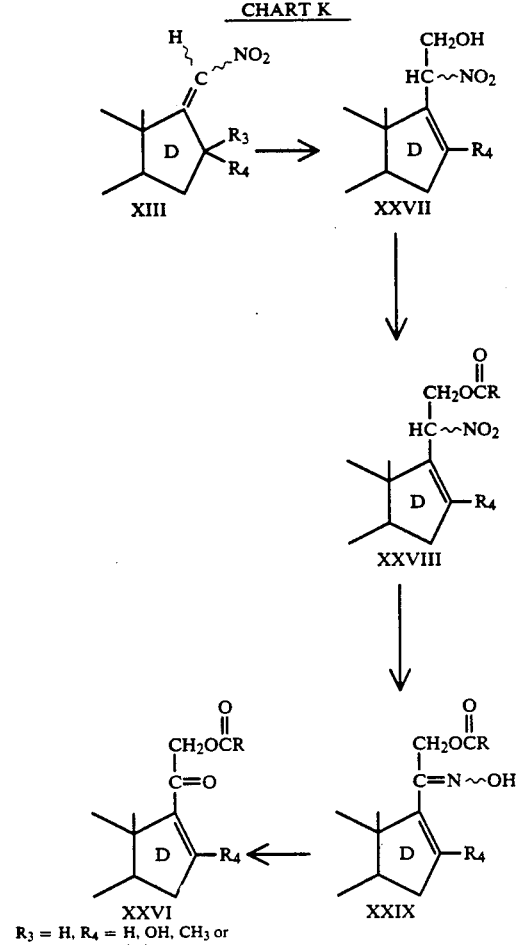
CHART L
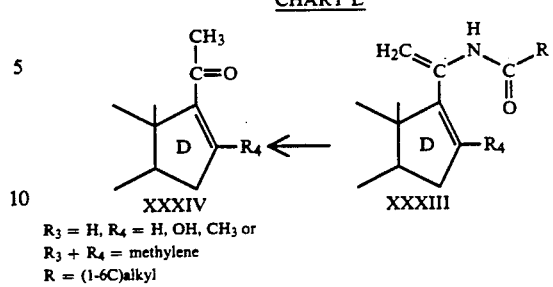
R₃ = H, R₄ = H, OH, CH₃ or
R₃ + R₄ = methylene
R = (1-6C)alkyl
CHART M
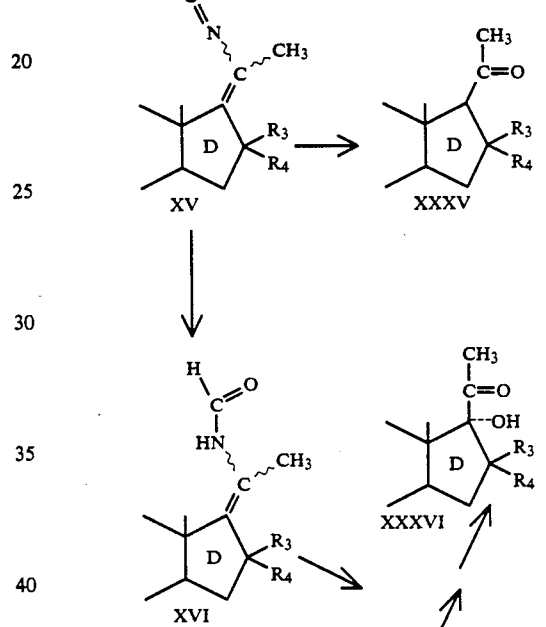
CHART L
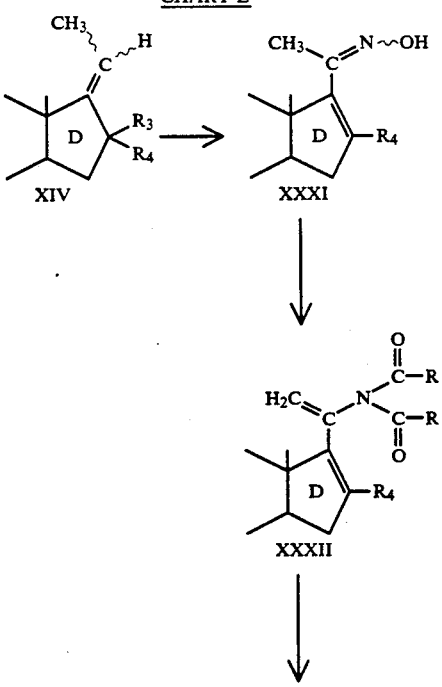
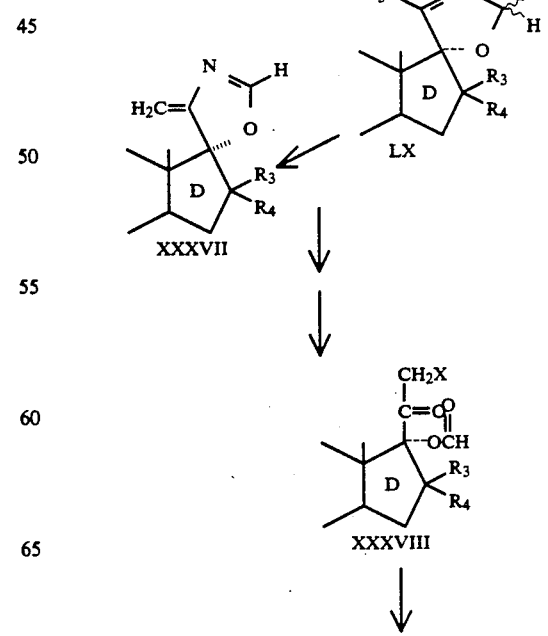

-continued
CHART M
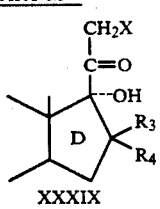
XXXIX
$R_3$ = H, H, $R_4$ = H, OH, $CH_3$ or
$R_3$ + $R_4$ = methylene
X = halogen
Chemical Formulas
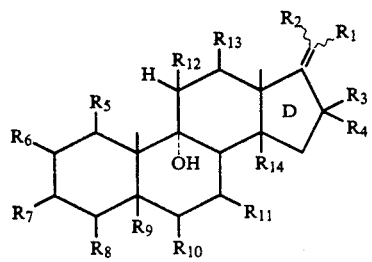   I
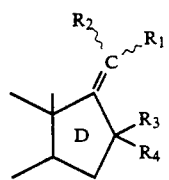   II
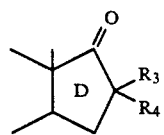   III
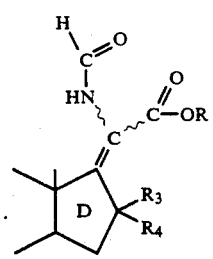   IV
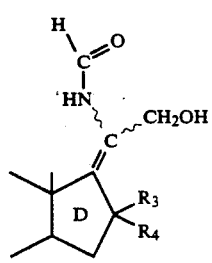   V
-continued
Chemical Formulas
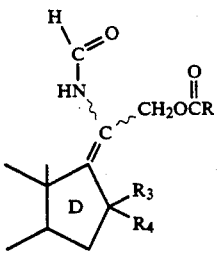   VI
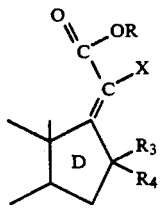   VII
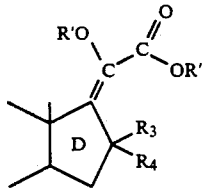   VIII
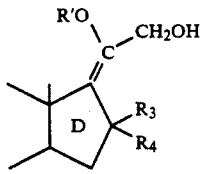   IX
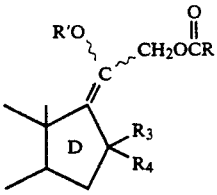   X
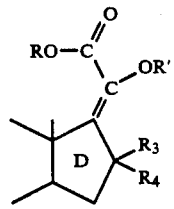   XI
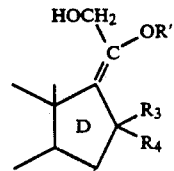   XII -continued
Chemical Formulas

XIII

XIV

XV

XVI

XVII

XVIII

XIX

-continued
Chemical Formulas

XX

XXI

XXII

XXIII

XXIV

XXV

XXVI

-continued
Chemical Formulas
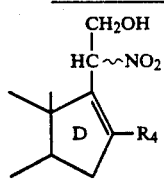 XXVII
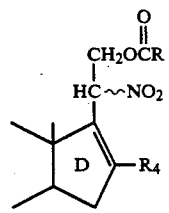 XXVIII
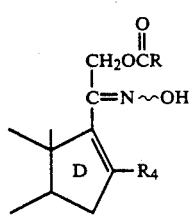 XXIX
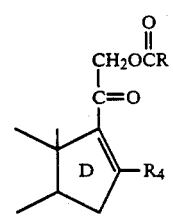 XXX
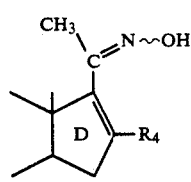 XXXI
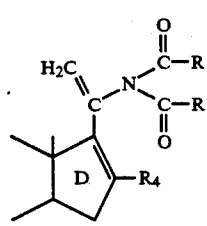 XXXII
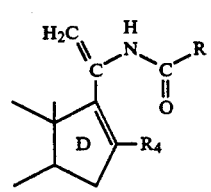 XXXIII
-continued
Chemical Formulas
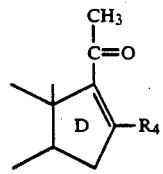 XXXIV
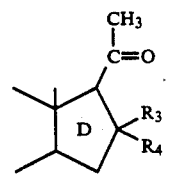 XXXV
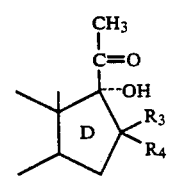 XXXVI
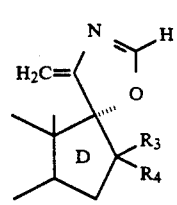 XXXVII
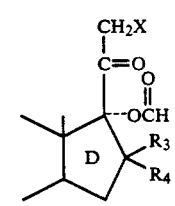 XXXVIII
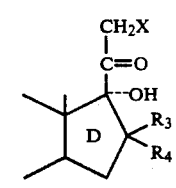 XXXIX
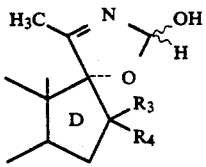 LX
We claim:
1. A 9α-Hydroxy-17-methylene steroid containing a D-ring according to formula I

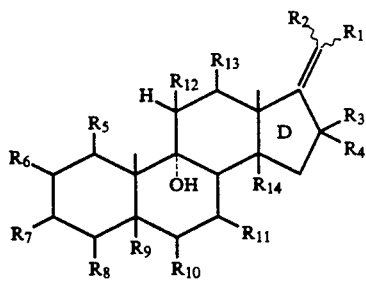

where
R$_1$ is hydrogen, halogen, cyano, isocyano, formamido, (1–6C) alkoxy,

R$_2$ is nitro, methyl, (1–6C) alkoxycarbonyl, hydroxymethyl, (1–6C) alkylcarbonyloxymethyl the 20-carbon atom being either in the Z- or in the E-configuration, R$_3$ is hydrogen R$_4$ is hydrogen, hydroxy, methyl or R$_3$ and R$_4$ together form methylene, R$_5$ is hydrogen, alkyl or with R$_6$ is a double bond, epoxy, methylene, 3,3-alkylenedioxy, 3,3-alkylenedithio or 3,3-alkyleneoxythio group, the alkylene group containing 2 or 3 carbon atoms, R$_6$ is hydrogen, alkyl or with R$_5$ is a double bond, epoxy, methylene, 3,3-alkylenedioxy, 3,3-alkylenedithio or 3,3-alkyleneoxythio group, the alkylene group containing 2 or 3 carbon atoms, R$_7$ is hydrogen, hydroxy, oxo, (1–4C) alkoxy, (1–6C) alkylcarbonyloxy, alkoxyalkoxy, tetrahydropyranyloxy, amino, 3-alkylamino containing 1 through 4 carbon atoms, 3-dialkylamino wherein the alkyl groups are the same or different, each alkyl group containing 1 through 4 carbon atoms, or 3-dialkylamino groups in which the nitrogen atom together with the alkyl groups forms a heterocyclic ring having 3 through 6 ring atoms, or 3-morpholino imino, 3-hydroxyimino, 3-(1–6C) alkoxyimino, 3,3-alkylenedioxy, 3,3-alkylenedithio, 3,3-alkyleneoxythio, the alkylene group containing 2 or 3 carbon atoms, or with R$_8$ is a double bond, R$_8$ is hydrogen or with R$_7$ or R$_9$ is a double bond, R$_9$ is hydrogen or with R$_8$ or R$_{10}$ is a double bond, R$_{10}$ is hydrogen, halogen or alkyl or with R$_9$ or R$_{11}$ is a double bond, R$_{11}$ is hydrogen, hydroxy or alkyl or with R$_9$ or R$_{11}$ is a double bond, R$_{12}$ is hydrogen, hydroxy, halogen, alkoxy, alkoxyalkoxy, tetrahydropyranyloxy or with R$_{13}$ is a double bond, R$_{13}$ is hydrogen, hydroxy, oxo, (1–4C) alkoxy or with R$_{12}$ is a double bond, R$_{14}$ is hydrogen or hydroxy, with the exception of 9α,21-dihydroxypregna-4,17-(20)-diene-3,11-dione and the corresponding 21-acetate.

2. A 9α-Hydroxy-17-methylene steroid according to claim 1 wherein when the steroid contains substituents having 3-oxo function, the steroid further contains a protecting group for protecting the 3-oxo function selected from the group consisting of (1–4C) alkyoxy, (1–6C) alkylcarbonyloxy, alkoxyalkoxy, tetrahydropyranyloxy, amino, 3-alkylamino containing 1 through 4 carbon atoms, 3-dialkylamino wherein the alkyl groups are the same or different, each alkyl group containing 1 through 4 carbon atoms, or 3-dialkylamino groups in which the nitrogen atom together with the alkyl groups forms a heterocyclic ring having 3 through 6 ring atoms, or 3-morpholino, 3-imino, 3-hydroxyimino, 3-(1–6C) alkoxyimino, 3,3-alkylenedioxy, 3,3-alkylenedithio, 3,3-alkyleneoxythio and the alkylene group containing 2 or 3 carbon atoms, either combined with a 4(5) double bond or not.

3. A 9α-Hydroxy-17-methylene steroid according to claim 1, where R$_1$ is formamido or cyano, R$_2$ is (1–6C) alkoxycarbonyl, hydroxymethyl or (1–6C) alkyl-carbonyloxymethyl.

4. A 9α-Hydroxy-17-methylene steroid according to claim 1 where R$_1$ is halogen or (1–6C) alkoxy, R$_2$ is (1–6C) alkoxycarbonyl, hydroxymethyl or (1–6C) alkycarbonyloxymethyl.

5. A 9α-Hydroxy-17-methylene steroid according to claim 1, where R$_1$ is hydrogen and R$_2$ is methyl or nitro.

6. A 9α-Hydroxy-17-methylene steroid according to claim 1, where R$_1$ is isocyano or formamido and R$_2$ is methyl.

7. A 9α-Hydroxy-17-methylene steroid selected from the group consisting of (1–6C)alkyl 20-formamido-9α-hydroxy-3-oxopregna-4,17(20)-dien-21-oate; 20-formamido-9α,21-dihydroxypregna-4,17(20)-dien-3one; (1–6C)alkyl 20-chloro-9α-hydroxy-3-oxopregna-4,17(20)-dien-21-oate; (1–6C)alkyl 20-(1–6C)alkoxy-9α-hydroxy-3-oxopregna-4,17(20)-dien-21-oate; 20-(1–6C-)alkoxy-9α,21-dihydroxypregna-4,17(20)-dien-3-one; 21-(1–6C)alkylcarbonyloxy-20-(1–6C)alkoxy-9α-hydroxypregna-4,17(20)-dien-3-one; 9α-hydroxy-17-nitromethyleneandrost-4-en-3-one; 9α-hydroxypregna-4,17-(20)-dien-3-one; 9α-hydroxy-20-isocyanopregna-4,17(20)-dien-3-one; 20-formamido-9α-hydroxypregna-4,17(20)-dien-3-one; (1–6C)alkyl-20-cyano-9α-hydroxy-3-oxopregna-4,17(20)-dien-21-oate, in which compounds the function on C3 may be properly protected and C16 may be substituted by a methyl, a methylene or a hydroxyl group.

* * * * *